US009199070B2

(12) United States Patent
Wegener et al.

(10) Patent No.: US 9,199,070 B2
(45) Date of Patent: Dec. 1, 2015

(54) FLUID FLOW CONDUITS AND APPARATUS AND METHODS FOR MAKING AND JOINING FLUID CONDUITS

(71) Applicant: Fenwal, Inc., Lake Zurich, IL (US)

(72) Inventors: Christopher Wegener, Libertyville, IL (US); Kyungyoon Min, Kildeer, IL (US); Mark Brierton, Cary, IL (US); Benjamin Kusters, Racine, WI (US); James Madsen, Kildeer, IL (US); William H. Cork, Lake Bluff, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 14/110,010

(22) PCT Filed: Dec. 12, 2012

(86) PCT No.: PCT/US2012/069103
§ 371 (c)(1),
(2) Date: Oct. 4, 2013

(87) PCT Pub. No.: WO2013/096038
PCT Pub. Date: Jun. 27, 2013

(65) Prior Publication Data
US 2014/0034230 A1  Feb. 6, 2014

Related U.S. Application Data

(60) Provisional application No. 61/578,690, filed on Dec. 21, 2011, provisional application No. 61/585,467, filed on Jan. 11, 2012, provisional application No. 61/617,745, filed on Mar. 30, 2012.

(51) Int. Cl.
*B29C 65/36*  (2006.01)
*B29C 65/02*  (2006.01)
(Continued)

(52) U.S. Cl.
CPC ............ *A61M 39/143* (2013.01); *A61M 39/14* (2013.01); *B29C 65/022* (2013.01);
(Continued)

(58) Field of Classification Search
CPC ................. B29C 66/91231; B29C 66/91933; B29C 66/954; B29C 65/02; B29C 65/04; B29C 65/34; B29C 65/36
USPC ............... 156/273.9, 256, 296, 304.2, 304.6, 156/308.4
See application file for complete search history.

(56) References Cited

U.S. PATENT DOCUMENTS 3,528,867 A * 9/1970 Heller, Jr. et al. .......... 156/272.4
3,968,195 A    7/1976 Bishop
(Continued)

FOREIGN PATENT DOCUMENTS

EP    0194873 B1    7/1991
EP    0507321 B1    10/1992
(Continued)

OTHER PUBLICATIONS

Definition of "Metallic", Merriam-Webster online dictionary, retrieved Apr. 6, 2014.*
(Continued)

*Primary Examiner* — Richard Crispino
*Assistant Examiner* — Elizabeth Bradford
(74) *Attorney, Agent, or Firm* — Cook Alex Ltd.

(57) ABSTRACT

Fluid flow conduits (14a, 14b) and apparatus (40) and methods for joining the conduits (14a, 14b), preferably in a sterile manner, are disclosed. Each conduit (14, 14b) has a polymeric open end that is sealed by a sealing member (26a, 26b) that may include a heating element (28). The polymeric end material is melted, the sealing members (26a, 26b) are moved to expose the melted open ends of the conduits (14a, 14b) and the ends are brought together to form a fused or welded connection (12) between the conduits (14a, 14b).

28 Claims, 9 Drawing Sheets

(51) Int. Cl.
| | |
|---|---|
| *B29C 65/34* | (2006.01) |
| *A61M 39/14* | (2006.01) |
| *B29C 65/30* | (2006.01) |
| *B29C 65/32* | (2006.01) |
| *B29C 65/20* | (2006.01) |
| *B29C 65/78* | (2006.01) |
| *B29C 65/48* | (2006.01) |
| *B29C 65/50* | (2006.01) |
| *B29C 65/00* | (2006.01) |

(52) U.S. Cl.
CPC .......... *B29C 65/203* (2013.01); *B29C 65/2015* (2013.01); *B29C 65/30* (2013.01); *B29C 65/32* (2013.01); *B29C 65/36* (2013.01); *B29C 65/7841* (2013.01); *B29C 66/1142* (2013.01); *B29C 66/5221* (2013.01); *B29C 66/5223* (2013.01); *B29C 66/52298* (2013.01); *B29C 66/5346* (2013.01); *B29C 66/543* (2013.01); *B29C 66/857* (2013.01); *B29C 66/91421* (2013.01); *B29C 65/3444* (2013.01); *B29C 65/3456* (2013.01); *B29C 65/3644* (2013.01); *B29C 65/3656* (2013.01); *B29C 65/4855* (2013.01); *B29C 65/5021* (2013.01); *B29C 65/5057* (2013.01); *B29C 66/0342* (2013.01); *B29C 66/3494* (2013.01); *B29C 66/5414* (2013.01); *B29C 66/71* (2013.01); *B29C 66/73115* (2013.01); *B29C 66/73141* (2013.01); *B29C 66/919* (2013.01); *B29C 66/91231* (2013.01); *B29C 66/91651* (2013.01); *B29C 66/91933* (2013.01); *B29C 66/949* (2013.01); *B29C 66/954* (2013.01)

(56) References Cited

U.S. PATENT DOCUMENTS

| | | | |
|---|---|---|---|
| 4,030,494 A | | 6/1977 | Tenczar |
| 4,157,723 A | | 6/1979 | Granzow et al. |
| 4,223,675 A | * | 9/1980 | Williams ................ 604/410 |
| 4,369,779 A | | 1/1983 | Spencer |
| 4,412,835 A | | 11/1983 | Spencer |
| 4,443,215 A | | 4/1984 | Smith |
| RE32,056 E | | 12/1985 | Granzow et al. |
| 4,619,642 A | | 10/1986 | Spencer |
| 4,673,400 A | | 6/1987 | Martin |
| 4,737,214 A | | 4/1988 | Leurink et al. |
| 4,753,697 A | | 6/1988 | Shaposka et al. |
| 4,770,735 A | | 9/1988 | Shaposka et al. |
| 4,793,880 A | | 12/1988 | Shaposka et al. |
| 4,828,557 A | | 5/1989 | Persidsky |
| 4,832,773 A | | 5/1989 | Shaposka et al. |
| 4,864,101 A | | 9/1989 | Shaposka et al. |
| 4,897,138 A | | 1/1990 | Shaposka et al. |
| 4,913,756 A | | 4/1990 | Shaposka et al. |
| 4,933,036 A | | 6/1990 | Shaposka et al. |
| 5,009,645 A | | 4/1991 | Silver et al. |
| 5,141,592 A | | 8/1992 | Shaposka et al. |
| 5,156,701 A | | 10/1992 | Spencer et al. |
| 5,158,630 A | | 10/1992 | Shaposka et al. |
| 5,182,440 A | | 1/1993 | Dufour et al. |
| 5,209,800 A | | 5/1993 | Spencer et al. |
| 5,244,522 A | | 9/1993 | Spencer et al. |
| 5,248,359 A | | 9/1993 | Shaposka et al. |
| 5,256,229 A | | 10/1993 | Spencer |
| 5,256,845 A | | 10/1993 | Schippers |
| 5,272,304 A | | 12/1993 | Been et al. |
| 5,279,685 A | | 1/1994 | Ivansons et al. |
| 5,342,345 A | | 8/1994 | Spencer |
| D355,848 S | | 2/1995 | Ivansons et al. |
| 5,397,425 A | | 3/1995 | Ivansons et al. |
| D357,926 S | | 5/1995 | Ivansons et al. |
| 5,518,575 A | | 5/1996 | Watanabe |
| 5,525,186 A | | 6/1996 | Ivansons et al. |
| 5,632,852 A | | 5/1997 | Ivansons et al. |
| 5,674,333 A | | 10/1997 | Spencer |
| 5,733,268 A | | 3/1998 | Spencer |
| 5,802,689 A | | 9/1998 | Sano |
| 5,855,731 A | | 1/1999 | Spencer |
| 5,858,016 A | | 1/1999 | Bacehowski et al. |
| 5,871,612 A | | 2/1999 | Spencer |
| 5,919,173 A | | 7/1999 | Spencer |
| 5,928,216 A | | 7/1999 | Spencer |
| 6,020,574 A | | 2/2000 | Ivansons |
| 6,026,882 A | | 2/2000 | Yamada et al. |
| 6,071,690 A | | 6/2000 | Spencer |
| 6,132,833 A | | 10/2000 | Spencer |
| 6,177,652 B1 | | 1/2001 | Ivansons |
| 6,341,637 B1 | | 1/2002 | Yamada et al. |
| 6,348,049 B1 | | 2/2002 | Spencer |
| 6,416,489 B1 | | 7/2002 | Booth |
| 6,460,592 B1 | | 10/2002 | Sano et al. |
| 6,463,979 B1 | | 10/2002 | Sano et al. |
| 6,485,593 B1 | | 11/2002 | Christoffersen |
| 6,596,122 B1 | | 7/2003 | Savitski et al. |
| 6,637,489 B1 | | 10/2003 | Spencer |
| 6,705,372 B2 | | 3/2004 | Sano et al. |
| 6,982,051 B2 | | 1/2006 | St. Onge et al. |
| 6,998,560 B2 | | 2/2006 | Ananthanarayanan et al. |
| 7,119,305 B2 | | 10/2006 | Sano et al. |
| 7,122,094 B2 | | 10/2006 | Baradon et al. |
| 7,223,262 B2 | | 5/2007 | Brehm et al. |
| 7,371,305 B2 | | 5/2008 | Sano et al. |
| 7,398,813 B2 | | 7/2008 | Ivansons et al. |
| 7,484,529 B2 | | 2/2009 | Yokota et al. |
| 7,657,996 B2 | | 2/2010 | Sano et al. |
| 7,722,733 B2 | | 5/2010 | Tomasetti et al. |
| 7,779,880 B2 | | 8/2010 | Sano et al. |
| 7,828,788 B2 | | 11/2010 | Brehm et al. |
| 7,938,454 B2 | | 5/2011 | Buchanan et al. |
| 7,964,048 B2 | | 6/2011 | Hlavinka et al. |
| 8,146,642 B2 | | 4/2012 | Landherr et al. |
| 8,162,021 B2 | | 4/2012 | Tomasetti et al. |
| 8,448,992 B2 | | 5/2013 | Min et al. |
| 2002/0174956 A1 | | 11/2002 | Sano et al. |
| 2003/0032942 A1 | * | 2/2003 | Theeuwes et al. ........... 604/537 |
| 2003/0201059 A1 | * | 10/2003 | Holman et al. ............... 156/155 |
| 2006/0005371 A1 | | 1/2006 | Sano et al. |
| 2006/0054275 A1 | | 3/2006 | Sano et al. |
| 2006/0054613 A1 | | 3/2006 | Sano et al. |
| 2006/0062948 A1 | * | 3/2006 | Kalishek .................... 428/34.9 |
| 2006/0144525 A1 | | 7/2006 | Sano et al. |
| 2007/0142960 A1 | | 6/2007 | Bolinger et al. |
| 2007/0225673 A1 | | 9/2007 | Brehm et al. |
| 2008/0009833 A1 | | 1/2008 | Corbin et al. |
| 2008/0017307 A1 | * | 1/2008 | Ong et al. .................. 156/307.1 |
| 2010/0133807 A1 | | 6/2010 | Bilstad et al. |
| 2010/0137826 A1 | | 6/2010 | Watts et al. |
| 2010/0213192 A1 | * | 8/2010 | Middleton et al. ............ 219/759 |
| 2014/0360668 A1 | | 12/2014 | Madsen |

FOREIGN PATENT DOCUMENTS

| | | |
|---|---|---|
| EP | 0723851 A2 | 7/1996 |
| EP | 0731540 B1 | 10/2004 |
| JP | S61290035 | 12/1986 |
| JP | H09150458 | 6/1997 |
| WO | WO 8202528 A1 | 8/1982 |
| WO | WO 2012/022635 A2 | 2/2012 |

OTHER PUBLICATIONS

Notification of Transmittal of the International Search Report, International Search Report and Written Opinion for PCT/US2012/069103 dated Feb. 28, 2013.

\* cited by examiner

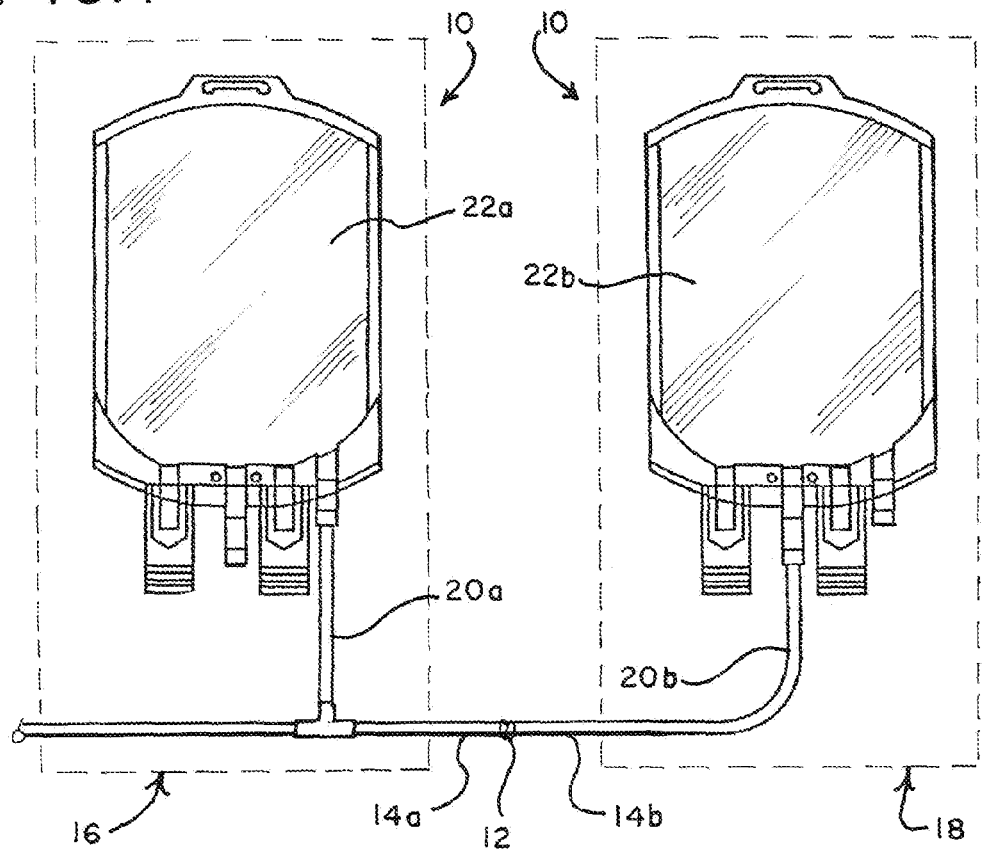
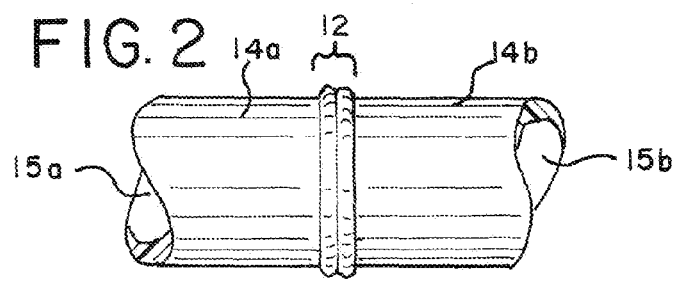
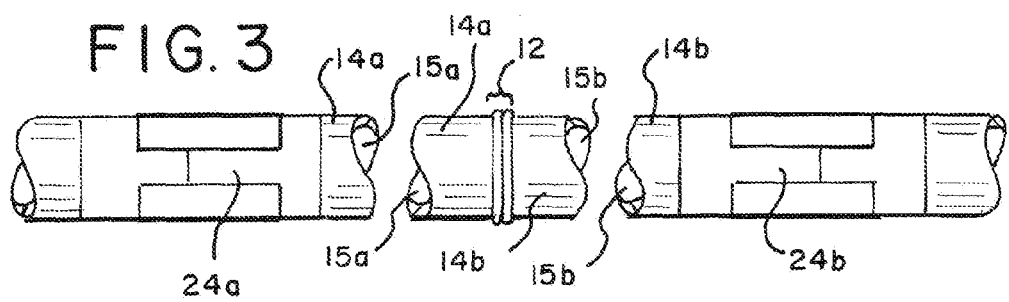

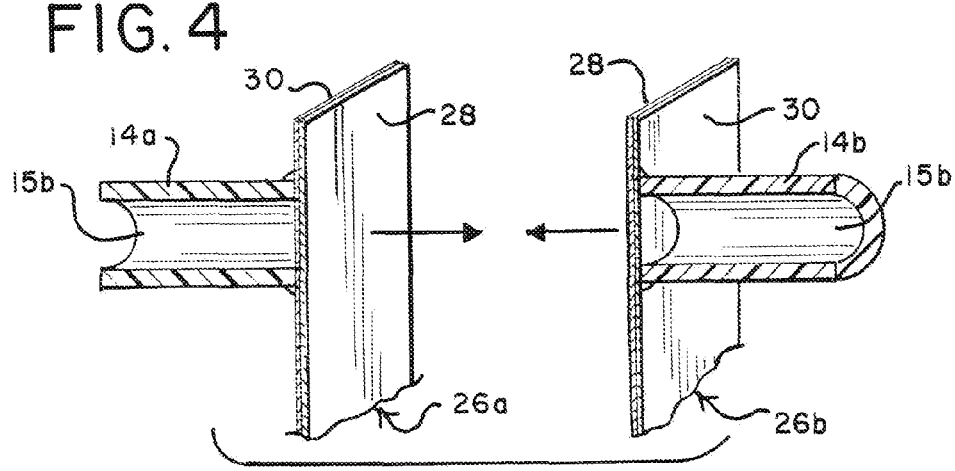
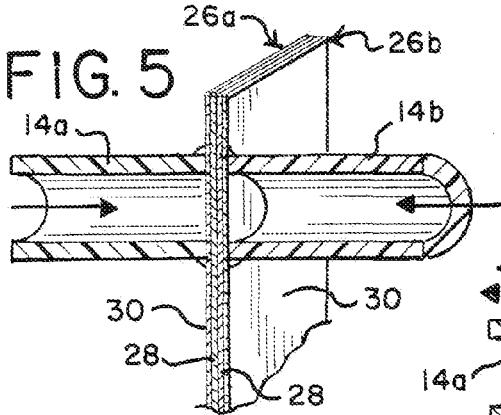
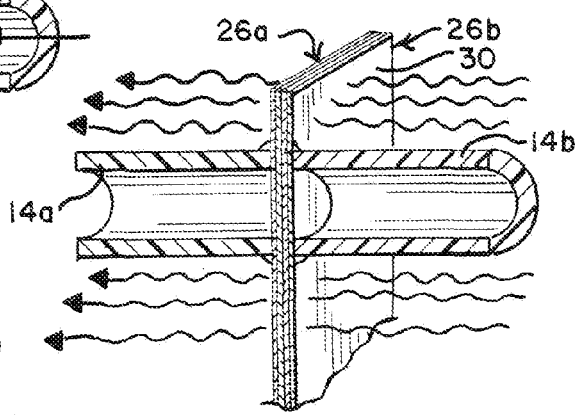
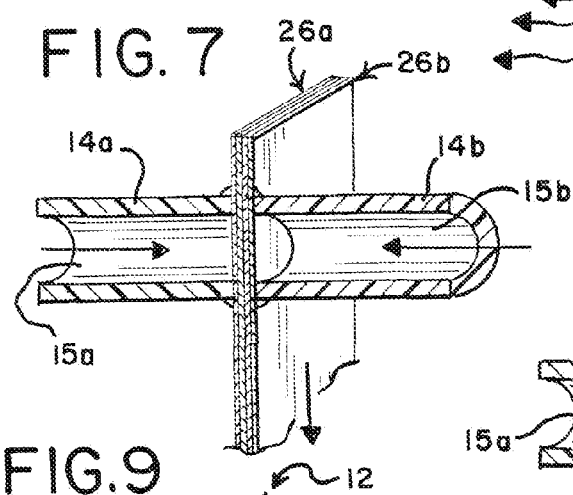
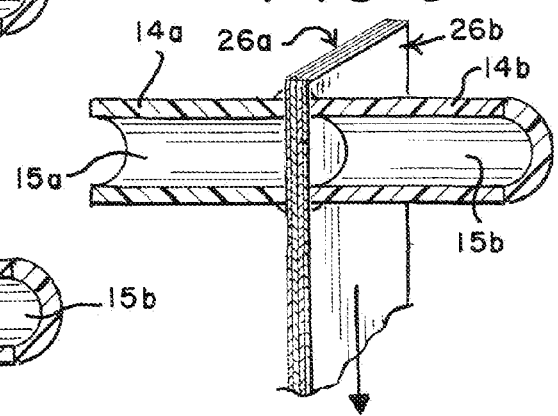
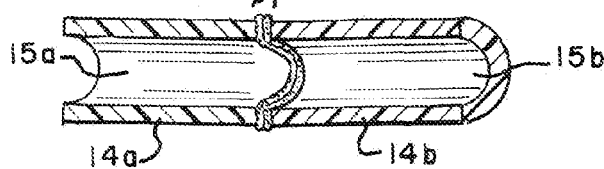

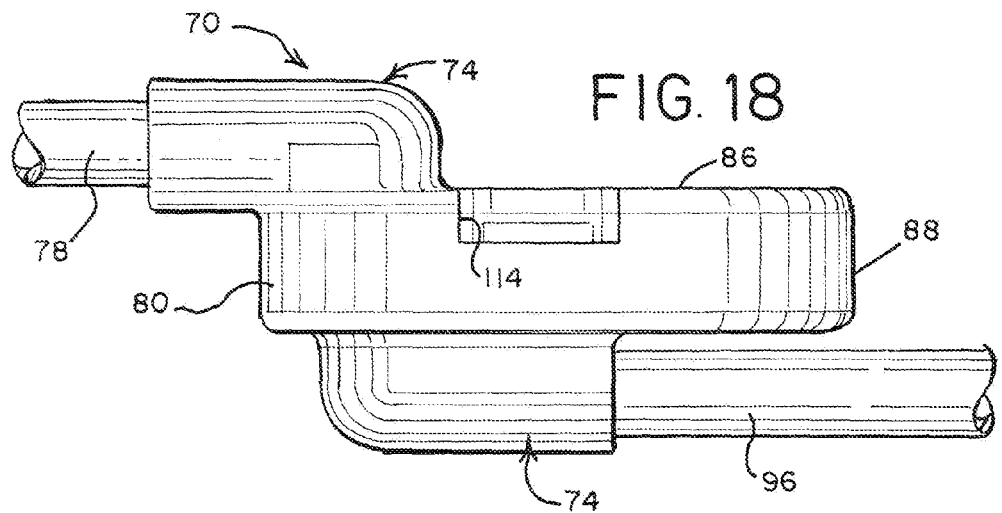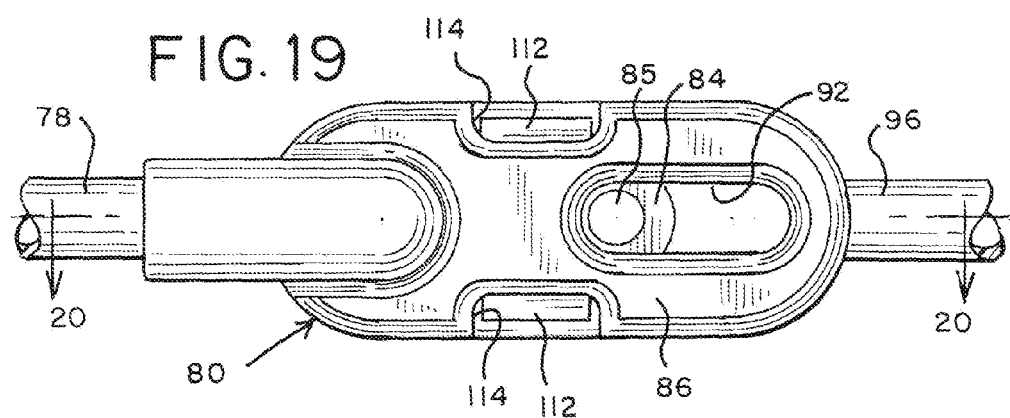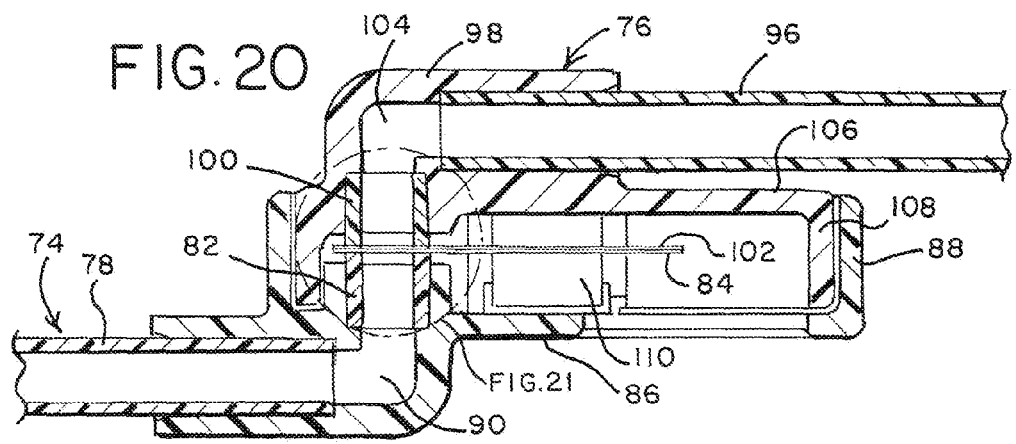

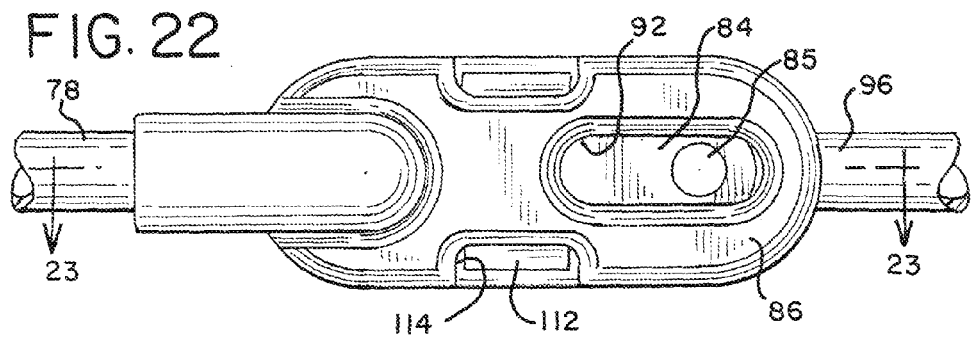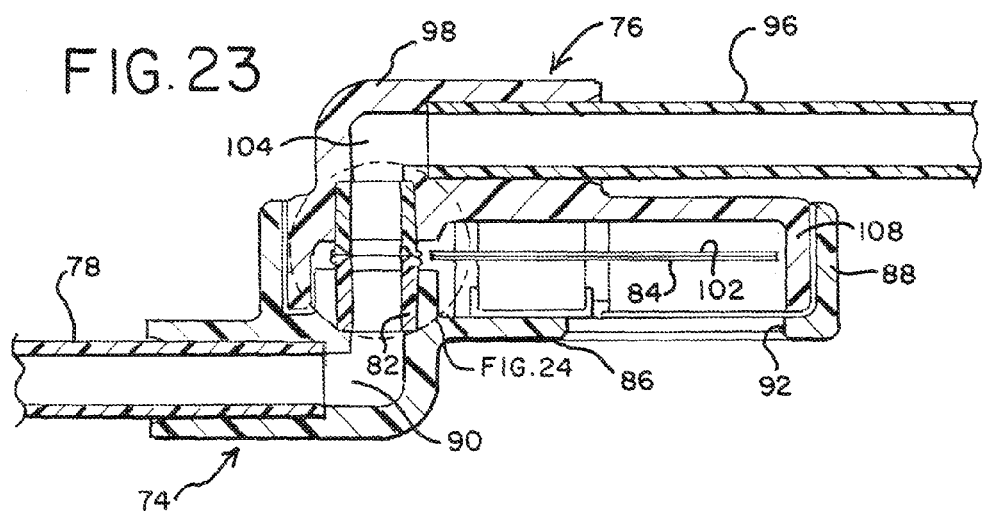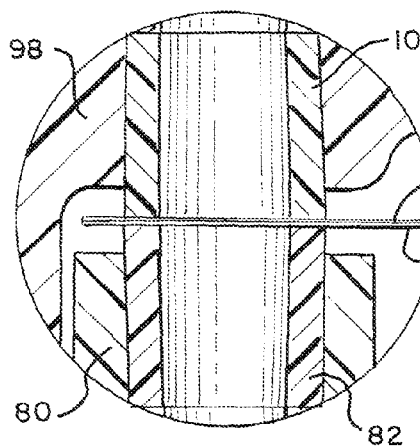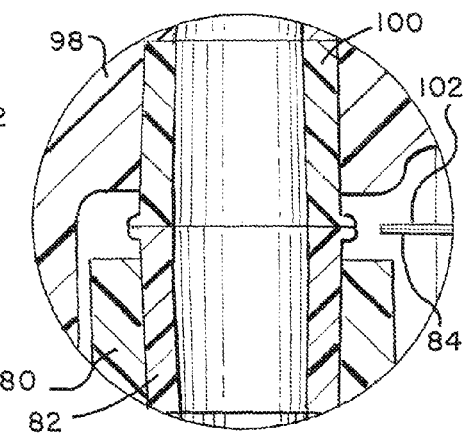

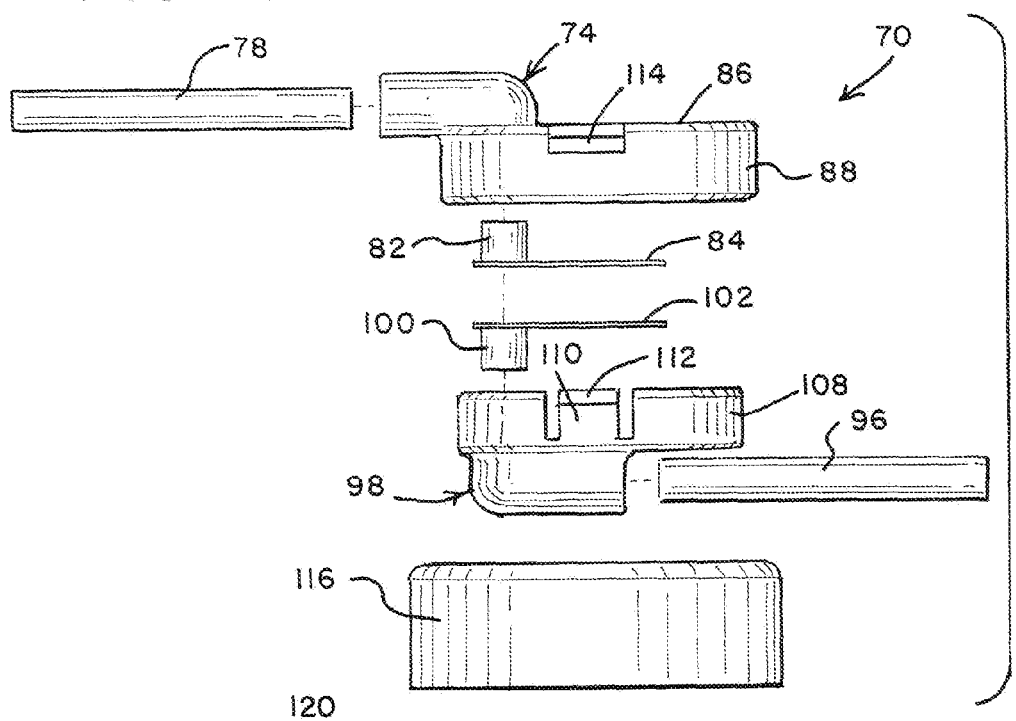
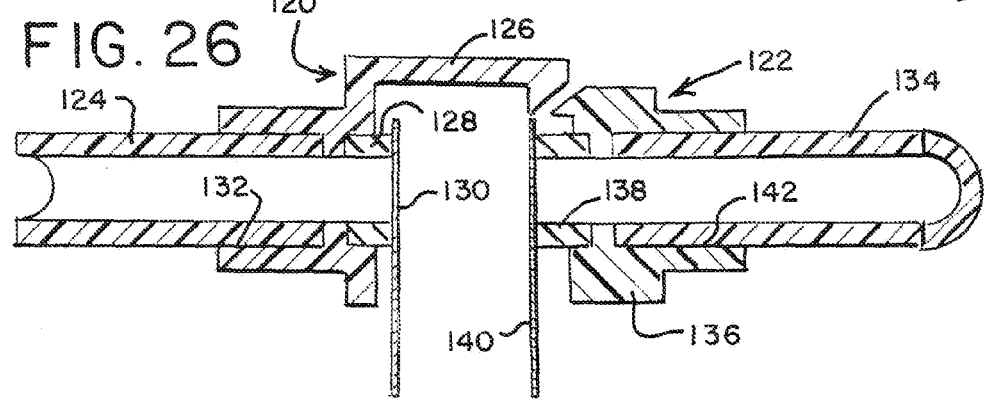
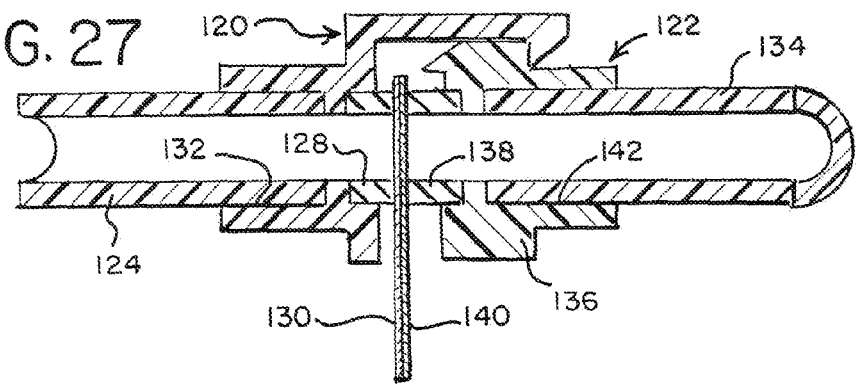

FLUID FLOW CONDUITS AND APPARATUS AND METHODS FOR MAKING AND JOINING FLUID CONDUITS

CROSS REFERENCE TO RELATED APPLICATIONS

This application claims priority to and the benefit of U.S. Patent Application Ser. No. 61/578,690 filed Dec. 21, 2011, U.S. Patent Application Ser. No. 61/585,467 filed Jan. 11, 2012 and U.S. Patent Application Ser. No. 61/617,745 filed Mar. 30, 2012, each of which is hereby incorporated by reference in its entirety.

TECHNICAL FIELD

The present disclosure relates generally to fluid flow systems and to apparatus and methods for assembling such systems. More particularly, but not exclusively, the present subject matter relates to sterile fluid flow systems, assemblies and subassemblies and to methods and apparatus for making connections, preferably sterile connections, in such systems

BACKGROUND ART

Fluid flow systems or assemblies that are pre-sterilized and/or pre-assembled are used in a wide variety of medical and non-medical applications. Medical applications may include, for example, administration of medical fluids to a patient for therapeutic and/or diagnostic purposes, blood and/or blood component or other cell collection or processing, dialysis and other medical procedures. Non-medical applications for such systems or assemblies may include, for example, pharmaceutical manufacturing and cell processing. In the medical field in particular, such flow systems commonly employ one or more pre-filled containers or other sources of medical fluid or agent and an associated fluid flow circuit or system (sometimes called a tubing set) containing the necessary flow tubing, valves, flow controllers, process chambers and the like to carry out the particular procedure, either alone or in cooperation with a reusable controller or other device. It is not unusual, for example, for a medical fluid flow system to include or be used in association with a container of a suitable drug, saline, anticoagulant, dextrose solution, sterile water, cell preservative or the like, to name just a few examples.

Such a fluid flow system can, however, pose manufacturing or assembly challenges for different reasons. One reason can be that the pre-filled containers of medical liquid, powder or other agent that is administered to the patient or otherwise employed in the medical fluid flow system, require different sterilization techniques than other portions of the fluid flow system. For example, empty plastic tubing, containers, flow control devices and/or processing devices or chambers, which do not contain any substantial amount of liquid or other agent, may be sterilized with gamma or electron beam (e-beam) radiation or by exposure to a sterilizing gas, e.g., ethylene oxide. However, gas sterilization would be ineffective to sterilize an agent, such as a liquid, powder or drug, contained in a sealed container, and exposing the agent to ionizing radiation may degrade or otherwise have a deleterious effect on the agent. Also, there may be situations where different portions of a sterile fluid flow system, even though suitable for the same sterilization process, are separately manufactured and sterilized for other reasons and then subsequently assembled in a sterile manner.

In addition sterile connections often need to be made on site, by the end user, e.g., at the location where the fluid flow systems are being used to treat patients or collect or process blood, or blood components, or biologic materials, or in other therapeutic or diagnostic procedures. For example, it may be desired to join a fluid source, filters, tubing or the like to other apparatus without compromising the sterility of any pre-sterilized components or parts of the assembly.

As a result of these various needs, a number of different approaches have been used in assembling sterile fluid flow systems. For example, one technique for manufacturing such systems employs the use of a sterile docking system, such as a device disclosed in U.S. Pat. No. 4,157,723. As illustrated there, the sterile docking system comprises a pair of mating members, each having a facing membrane. One of the mating members is connected to a pre-sterilized container of liquid, drug or other agent and the other mating member is attached to a pre-sterilized fluid flow system, which may include one or more empty containers. After the two members are joined, the docking system is exposed to radiant energy, causing the membranes to melt and form a sterile fluid pathway through the mating members. Fluid may then be transferred from the initial container into an empty container in the fluid flow system, and the flow path sealed and severed. The initial container and mating members are then discarded. While this works satisfactorily, it entails multiple manufacturing steps of transferring solution from one container to another in a sterile manner and the associated quality control procedures with such a step. It also requires the disposal of a portion of the product with increased product and waste cost.

Another technique for assembling medical fluid flow assemblies that have different pre-sterilized portions, such as the type requiring different sterilization processes, employs an electron beam. This technique, as described in U.S. Pat. No. 5,009,645, requires a manufacturing procedure employing an electron beam or the like to sterilize isolated portions of subassemblies after they have been joined together. After the isolated regions are joined and sterilized, clamps or frangible closures which isolate the regions may then be opened to allow for direct sterile communication between the subassemblies. Such a procedure and the use of e-beam or similar radiation, of course, requires a substantial investment in manufacturing equipment as well as additional procedures and safeguards during manufacture.

To avoid the use of more complicated manufacturing processes, it has also been disclosed to use sterilizing filters on the inlet flow line that couples a pre-sterilized liquid container or the like to a separately sterilized fluid flow tubing system. Such an arrangement is illustrated in U.S. Pat. No. 4,978,446. In the approach in the '446 patent, however, the medical personnel are required to manually join the fluid flow tubing system to the fluid container, such as by spiking the fluid container with a piercing member associated with the fluid flow system. In addition to the administrative requirements for individually ordering, storing and prescribing solutions and disposable flow systems or sets, there is the added possibility of errors, such as by connection of a container of an incorrect liquid or other agent or an improper flow system to be used in association with the procedure.

Also, there is a known device commonly referred to as sterile tubing welder that is marketed by Terumo Medical Corporation as the "SCD Device." That device uses a heated wafer to slice and melt the ends of tubing, which are joined together after the wafer is removed. Aspects of this device are disclosed in various patents, including U.S. Pat. Nos. 4,753, 697, 5,158,630 and 5,156,701. Although widely used, particularly as an "on-site" tool to allow users to assemble a system in such configuration as they desire, this device requires the use of expensive wafers that are replaced after each splice.

Sterile connection systems using a melting process are found in WO 2008/131442 A2 and WO 82/02528 and a sterile connection system using a movable internal wall and limited sterilization is found in U.S. Pat. No. 4,030,494.

Accordingly, there remains a significant need for advancements in this field.

SUMMARY

The present subject matter, as recited in part in the attached independent claims, is summarized below for purposes of introduction only. This summary is not intended to be a full or complete summary or listing of all aspects or of the broadest aspects of the present subject matter, and is only presented to acquaint the reader with the subject matter hereof, which is set forth more fully in following description and in the appended claims. The subject matter of this description has numerous separate and independent aspects including fluid flow conduits, circuits and assemblies, individual and assembled, methods and apparatus for making such conduits and assembling them and unique components employed in such conduits and their joinder. Accordingly, the headings used herein are only to guide the reader, and do not mean that the description under a particular heating is limited to or only pertains to the specific subject matter of the heading.

In one aspect, a method is provided for joining first and second fluid flow circuits or subassemblies to form a fluid flow circuit assembly. Each fluid flow circuit or subassembly includes a fluid flow conduit with a lumen and an open end terminating in a heat meltable material, such as a polymeric material, that softens or melts when heated and hardens upon cooling and a sealing member attached to the flow conduit and preferably sealing the open end thereof. At least one of the sealing members includes at least one heating element. The method includes: (a) melting the material of the open ends by heating the at least one heating element; (b) relatively moving the sealing members and the respective open ends to which they are sealed to expose the open ends; and (c) bringing the exposed open ends together while melted to form a junction between the fluid flow circuits that allows fluid flow therebetween. Although the sealing member is typically referred to as closing or sealing the fluid flow conduit, for junctions where sterility or sterile connection is not required, the sealing member need not seal the open end of the conduit from ambient conditions.

In another aspect, a method is provided for making a fluid flow conduit that may be employed with other aspects of the present subject matter. The method includes providing hollow tubing having a lumen and a meltable distal end, and bonding the distal end of the tubing to a sealing panel that includes a heating element or member, which sealing panel hermetically seals the tubing. The distal end material may be a polymer or other suitable material as explained below. The panel can have one or more layers, as in a laminated web or film for example.

In yet a further embodiment, a unique fluid flow circuit or subassembly is provided. The fluid flow circuit includes a fluid conduit having a lumen and at least one open end terminating in a heat meltable end material (e.g., a polymer material) and a sealing member sealing the open end of the conduit. The sealing member includes at least one heating element configured to melt the end material upon energizing, and the sealing member and open end of the conduit are relatively movable to a non-sealing position upon heating to expose the molten end material.

In another aspect, a fluid flow circuit assembly is provided comprising first and second separate fluid flow circuits or subassemblies, each of which includes: (i) a fluid conduit including a lumen and at least one open end terminating in a heat meltable end material (such as a polymeric material); (ii) a sealing member sealing the open end of the conduit; (iii) the sealing member including at least one heating element configured to melt the end material upon energizing; (iv) the sealing member being movable to a non-sealing position upon heating to expose the molten end material; and (v) a housing carrying the sealing member. The housings of the first and second flow circuits or subassemblies are configured for irreversible connection to one another with the sealing members of each circuit being cooperatively in contact with one another with the end material of each conduit being in compression, such that upon heating of such sealing members to melt the end material of each conduit and movement of the sealing members to expose the molten end materials, the molten ends engage together to form a sealed junction therebetween.

In a still further aspect, connection apparatus is provided for joining two fluid flow circuits or subassemblies of the type comprising: a fluid conduit including a lumen and at least one open end terminating in a heat meltable end material (e.g., a polymeric material); a sealing member sealing the open end of the conduit; the sealing member including at least one heating element configured to melt the end material upon energizing; and the sealing member and open end of the conduit being relatively movable to a non-sealing position upon heating to expose the molten end material. The connection apparatus includes: (a) opposed conduit holders, each of which is configured to hold a portion of one of the fluid flow circuits or subassemblies, with the open ends generally in axial alignment. The conduit holders are relatively movable to move the sealing members toward each other to hold them in contact with each other. The connection apparatus also includes a power source for heating at least one of the heating members sufficiently melt the end material of the respective flow circuits and a sealing member holder configured to hold the sealing members. The sealing member holder and the conduit holders are respectively laterally movable to move the sealing members from between the open ends when the end material is melted.

In a still further aspect, a method of joining first and second fluid flow conduits is provided. Each of the conduits includes a lumen and an open end terminating in a heat meltable material (e.g., polymeric material) and a sealing member attached to the flow conduit and sealing the open end thereof, and each of the sealing members includes at least one heating element. The method includes: (a) placing the sealing members in face to face contact; (b) melting the material of the open ends by heating the at least one heating elements of each sealing member; and (c) moving the sealing members from between the respective open ends of the conduits while pressing the open ends of the conduits toward each other to bring the exposed open ends together while melted to form a junction between the fluid flow conduits that allows fluid flow therebetween.

DESCRIPTION OF DRAWINGS

These and other aspects are disclosed in the following detailed description and accompanying drawings, of which:

FIG. 1 is a plan view of an exemplary fluid flow assembly formed by joining flow conduits of two fluid flow circuits or subassemblies employing certain aspects of subject matter of this description.

FIG. 2 is a side view of the connection junction or union formed in accordance with the present subject matter between two fluid conduits.

FIG. 3 is a side view of a conduit connection junction or union such as shown in FIG. 2 and in which at least one and preferably both fluid conduits include internal frangible closures to control flow.

FIGS. 4-9 are partial perspective views of two fluid conduits (which may be part of larger fluid circuits or subassemblies), which in accordance with the present disclosure are being connected, preferably in a sterile manner.

FIG. 18 is a side view of an alternative connection assembly connecting two fluid conduits (which may be part of larger circuits or subassemblies) in accordance with another aspect of the present subject matter.

FIG. 19 is a top view of the connection assembly of FIG. 18.

FIG. 20 is a cross-sectional view taken along lines 20-20 of FIG. 19 before the conduits are connected in fluid flow relation.

FIG. 21 is an enlarged view of the connection detail in FIG. 20.

FIG. 22 is a top view of the connection assembly of FIG. 18 after the fluid flow circuits are connected in flow relation.

FIG. 23 is a cross-sectional view taken along lines 23-23 of FIG. 22.

FIG. 24 is an enlarged view of the connection detail in FIG. 23.

FIG. 25 is a side exploded view of the connection assembly of FIG. 18, also showing an induction power source mounting fixture for the assembly.

FIG. 26 is sectional view illustrating another embodiment of a connection assembly and method for joining two fluid flow conduits employing certain aspects of subject matter of this description and showing the conduits before connection.

FIG. 27 is a sectional view of the assembly of FIG. 26 in the attached configuration and before the union between the conduits is formed.

DETAILED DESCRIPTION

Figure 10:
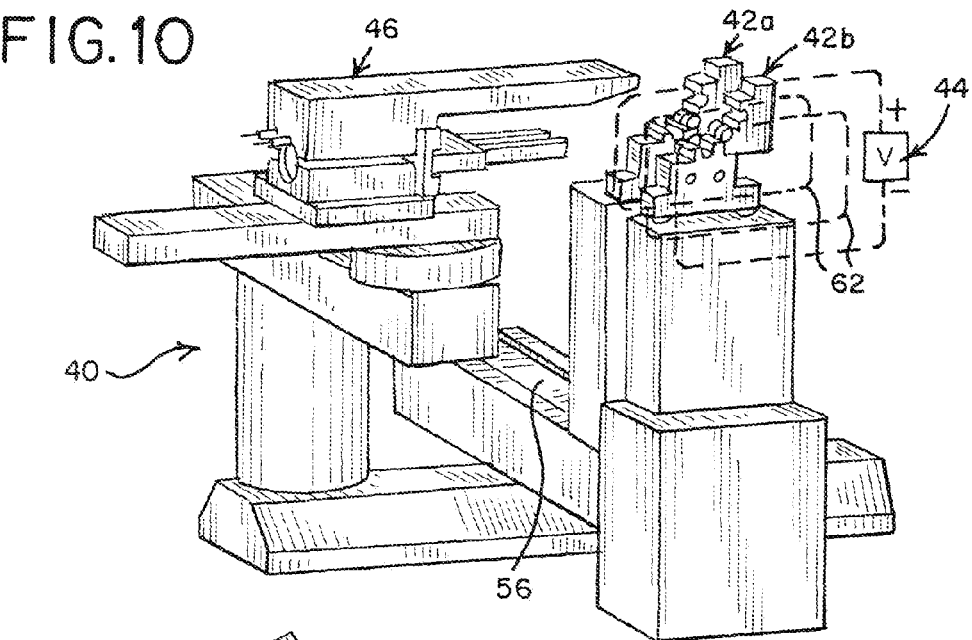
FIG. 10 is a side perspective view of an exemplary apparatus that may be employed in connecting two fluid flow conduits in accordance with the present subject matter.

FIG. 1 illustrates one example of a fluid circuit assembly 10, including a connection or union 12 joining two fluid flow conduits 14a,b, which are illustrated as part of first and second fluid circuits or subassemblies 16 and 18, respectively, to form the fluid circuit assembly 10. Each fluid flow circuit or subassembly 16 and 18 may include additional tubing, containers, valves, separation chambers, and other selected fluid processing or storing apparatus as desired for the particular application. As illustrated, each circuit or subassembly the fluid conduits 14a,b of each may include one or more tubing fluid flow paths 20a,b and fluid containers 22a,b, but the exact components of each circuit or subassembly may vary as the use requires, and fluid containers are optional in one or both fluid circuits.

The present subject matter has potential application in a wide variety of environments, industries and applications. In its broader aspects, it is not limited to making sterile connections. However, it will be appreciated that it has particular application and benefit in making sterile connections between pre-sterilized conduits, flow circuits or subassemblies of a sterile fluid flow assembly or system, such as a disposable sterile medical fluid flow assembly. Such sterile fluid flow systems may be found in any of a variety of medical and non-medical applications and systems such as (1) administration or withdrawal of fluid to or from a patient for any diagnostic or therapeutic purpose, (2) collection, storage or processing of blood or blood components or other cells or cellular materials, (3) blood separating and/or collecting systems for use with hardware such as supplied by Fenwal Inc., Caridian, Inc and/or Haemonetics Inc., (4) pharmaceutical manufacturing, (5) cell culturing and/or (6) other sterile fluid flow system applications where collecting, storing or processing of fluid is desired, whether or not the system is directly attached to a human or animal.

In one non-exclusive example, such fluid circuit assembly 10 may be configured for employment in the collection or processing of blood or blood components, and may comprise a preassembled, sterile, disposable medical fluid flow system such as the type that may be associated with the ALYX Centrifugal Blood Processing System sold by Fenwal, Inc. of Lake Zurich, Ill., and illustrated in more detail, for example, in U.S. Pat. No. 6,322,488, which is hereby incorporated by reference. The ALYX system is referred to only for purposes of illustration of one type of a medical fluid flow system, and the present subject matter may be employed in any of a wide variety of sterile fluid flow systems in general and disposable pre-sterilized fluid flow systems in particular.

As noted above, the present subject matter has particular application to sterile disposable medical fluid flow systems (e.g., assembly 10), that are assembled by joining fluid circuits or circuit subassemblies (e.g., fluid flow circuits 16 and 18) that are pre-sterilized and subsequently joined together in a sterile manner to provide a sterile fluid circuit assembly of a desired configuration. This has application, for example, where the first or second fluid flow circuits are separately pre-sterilized because one includes a therapeutic, diagnostic or other agent that is not suitable to undergo the same sterilization process as the other fluid flow circuit. For example, a fluid flow circuit that is "wet" (includes a sealed container of drug or other liquid) may require steam or heat sterilization, whereas a fluid flow circuit that is "dry" (includes only empty tubing, containers and the like) may be efficiently gas or radiation sterilized. Other factors may also dictate the type of sterilization, such as the materials or configuration, contents or ultimate use of the fluid flow circuit. In addition, the present subject matter has application where the first or second fluid flow circuits are separately manufactured and pre-sterilized for reasons other than sterilization, such as convenience, manufacturing efficiency, marketing, user flexibility in assembling the desired fluid flow circuit assembly on site and/or other reasons.

Referring back to FIG. 1, it is within the scope of this description that the first and second circuits 16 and 18 may include additional parts or pieces of the overall system assembled in any desired way. Also, the circuits 16 and 18 may themselves be part of a larger system or systems, the other portions of which are assembled in a different manner than described herein, and which are not necessarily pre-assembled in their entirety. Nor does this description preclude the possibility that other components are subsequently attached to or associated with circuits 16 and 18, or are added to the overall system, in a manner different than described or claimed herein.

FIG. 2 is an enlarged view of the connection or union 12 formed between the fluid flow conduits 14a,b of the respective circuit or subassembly 16, 18. The connection, as described in more detail below, is specifically a union in which the open ends of the conduits weld or fuse together while melted to provide a permanent sealed junction between the conduits (and any associated fluid circuits or subassemblies) that is open sufficiently to allow fluid flow therebetween. As illustrated and preferred, the connection 12 is sufficiently strong so as not to require any other connecting structure or reinforcement and is preferably solely a weld or fusion bond between the open conduit ends.

As described in more detail below, to achieve this welded or fused connection, each conduit 14a,b terminates in an open end that is made of a material, such as a thermoplastic polymeric material, that softens sufficiently when heated to allow the formation of a weld or fusion bond between the conduits and hardens when cooled. In a preferred configuration, the conduits each terminate in a thermoplastic polymeric material, preferably flexible and resilient, such as polyvinyl chloride (PVC), polypropylene (PP) or other polymeric material that becomes sufficiently softened and amorphous when heated to allow the formation of a fusion bond or weld between the material at the ends of the conduits when they are brought together, and hardens when cooled. For purposes of this description, this softening is referred to as "melting," and the conduit ends may be referred to as melted or molten—although it is understood that for thermoplastic polymeric material this "melting" is more of the nature of a transition from a crystalline phase to an amorphous phase than an abrupt solid-liquid transformation. References to polymeric material herein will be understood to refer to thermoplastic polymeric material, which exhibits the above properties.

Turning to FIG. 3, although the conduits 14a,b leading to the connection may be open for fluid flow immediately after the connection 12 is made, as shown in FIG. 3 it is also contemplated the one or both conduits may include an internal frangible closure 24a,b. Frangible closures that can be opened by external manipulation, without breaching sterility, such as by manual or automated flexing or bending of the conduit tubing, are well known in the medical industry. Examples of such frangible closures may be found in, inter alia, U.S. Pat. Nos. 4,340,049; 4,181,140 and 5,330,464 which are hereby incorporated by reference. With the frangible closures 24a,b in one or both conduits 14a,b, the user may confirm the integrity of the connection 12, if desired, (for example, by performing a pull test) before allowing fluid to flow through it by opening the frangible closures.

FIGS. 4-9 diagrammatically illustrate the formation of the connection 12 between the conduits 14a,b of respective fluid flow circuits or subassemblies 16 and 18. As noted earlier, the fluid flow circuits or subassemblies may have any suitable configuration or components, with or without fluid containers. FIGS. 4-9 show only the terminal end of the conduits 14a,b for simplicity and ease of illustration of the formation of connection or junction 12. The illustrated conduit portions may, for example, be terminal tubing segments specifically selected for connection as described herein, or continuation of tubing used throughout the respective fluid circuit or subassembly. As shown in FIGS. 4-9, each conduit has an internal lumen or bore 15a,b defining a fluid flow path. The open end of the lumen or bore of each respective conduit 14a,b has attached thereto a sealing member 26a or 26b, respectively. The sealing member preferably closes the end of the conduit and, if the conduit is pre-sterilized, seals the conduit to preserve the sterility thereof.

Sealing Member

The sealing members 26a,b may be of any suitable configuration, shape or size and attached to the open end of the conduits 14a,b by adhesive, solvent or heat weld, and may be of the same or different configuration or materials. As described in more detail below, the sealing member may include at least one heating element that, during the connection procedure, is heated to an elevated temperature that causes the material at the open ends of the conduits to melt. For making sterile connections between pre-sterilized fluid flow circuits or subassemblies 16 and 18 the elevated temperature is preferably sufficiently high to cause sterilization of the sealing members or at least those portions of the sealing members that are exposed to the sterile lumen of the conduits.

More specifically, each sealing member 26a,b is not limited to a single element or device, but can be an assembly of multiple parts and pieces including, if desired, the heating member or element (which likewise can be more than one part or piece). As shown in FIG. 4, the illustrated sealing members are each configured as a relatively thin panel, such as a thin web or film, that may be of a single layer or multiple layers, such as two, three or more layers or coatings or laminations. The illustrated sealing member is a panel having two layers 28 and 30.

As depicted, layer 28 may be an electrically conductive material, such as a conductive polymer or conductive metal, which functions as a heating member. If metallic, layer 28 may be a film or foil made single material, such as copper, aluminum, stainless steel, brass, bronze, gold or silver, or an alloy thereof, or include multiple thicknesses or layers of different metallic materials if desired. Also, metallic layer 28 may have such surface treatment, coatings or addition layers for such other purposes as may be desired, such as protection against oxidation. For purposes of this description, "film" and "foil" are used interchangeably. Although FIGS. 4-9 show each sealing member with two layers, one of which is a conductive layer, it is understood that the sealing members are not required to have the identical construction, although that may be preferred from a manufacturing standpoint. Also, it is not required that each sealing member include a heating element, although that too may be preferred.

The electrically conductive material acts as a heating member, and when energized, such as by electrical induction, direct electrical voltage application, radiofrequency energy or microwave, heats to an elevated temperature. At present, inductive heating of the conductive material by applying a magnetic field is preferred, in part because it does not require physical contact between the heating element and power source, whereas resistive heating via direct application of voltage to the conductive material is an alternative. Microwave heating also the advantage that it does not require physical contact between the heating element and power source. If microwave heating is used, a coating of suitable material may be employed on the film or foil to better distribute the microwave energy.

The conductive layer 28, if a metallic conductor, preferably has a thickness not substantially greater, and preferably less than or equal to about its "skin depth" for the respective electrical frequency of the current-inducing voltage used. However, thicknesses greater or less than skin depth may be used if desired for other reasons, such as ease of fabricating or handling or for use with other power sources. For example, if the skin depth of a particular metal at the frequency of a given electrical induction generator is so small that a metallic film of such thickness is too fragile for efficient handling in a manufacturing setting, the layer of such material may be thicker than the skin depth. Alternatively, a different metallic material and/or a different power source frequency may be selected to optimize material usage, connection efficiency and/or product cost.

For reference purposes only, the side or surface of the sealing element 26a, b that faces the respective terminal conduit segment 14a,b to which it is attached is referred to as proximal, and the side or surface facing away from the conduit segment is referred to as distal. As presently contemplated, the proximal surface of the illustrated multi-layer panel sealing member 26a,b, or a portion of the proximal surface is made of or includes a layer or coating 30 of a material that is compatible with and suitable for bonding to the respective conduit in order to seal the open end of the conduit. For example, the sealing member panel 26a,b may include a PVC layer or coating that can be directly bonded to a PVC terminal end material of the conduit. If the end of the conduit is made of other material, such as polypropylene (PP), a proximal coating or layer of the different material (e.g., PP) may be required. It should be noted that the two layer panel of FIGS. 4-8 is only exemplary, and there may be only a single layer, such as a metallic film, or there may be additional layers such as one or more intermediate layers between the proximal layer or coating that bonds to the conduit and the conductive layer. There may also be additional layers or coatings proximal or distal of the conductive layer as well and/or there may be more than one conductive layer. For example, if it is desired to have a PVC or PP proximal layer for bonding to the conduit 14a,b, and the material selected for the conductive layer does not bond well to PVC or PP, an adhesive layer may be provided between the distal conductive layer and a proximal PVC or PP layer. Layers of adhesive or other suitable material may make up one or more others layers of the sealing member, as desired. Most preferably, these materials are biocompatible for use in medical devices and are non-toxic and do not cause toxic emissions upon heating.

Another alternative sealing member includes layer of aluminum, copper or stainless steel foil having a thickness of about 0.0005 to about 0.005 inches (0.013-0.13 mm), and a PVC or other thermoplastic layer. The PVC layer may be formed by applying a PVC emulsion to the proximal surface of the foil. The total thickness of each laminate may be about 0.002 to about 0.008 inches, and typically less than 0.01 inches.

As noted earlier, the sealing members are preferably relatively thin. As a panel, which may be one or more layers, the thickness of the sealing members may be selected for the appropriate application. For example, a panel thickness may be less than or equal to about 0.02 inches (0.5 mm), or for making a sterile connection, as described below, the sealing member may preferably be less than about 0.01 inches (0.25 millimeters) thick and may, for example, between about 0.002 inches (0.05 mm) and about 0.007 inches (0.18 mm). The panel may also be thicker or thinner as desired.

Sealing Member/Conduit Attachment

As can be seen in FIGS. 4-8, the illustrated sealing members 26a,b are each a panel of elongated rectangular shape and preferably but not necessarily bonded to the end of the respective conduit 14a,b at a location, such as an offset location, nearer to one end of the panel. This positioning leaves the remaining portion of the panel available for ease of grasping, gripping or otherwise engaging, for purposes described later.

As described above, the material defining the open end of each conduit 14a,b is of a suitable heat meltable material, e.g., thermoplastic polymer, such as PP or PVC. To avoid excessive melting of the end of the conduit 4, when making a sterile connection as described below, the conduit material may be preferably selected to have a melt temperature approaching or exceeding the sterilizing temperature. PP, for example, typically has a higher melt temperature than PVC and may be preferred in certain applications. This will be explained in greater detail below.

As shown in FIG. 4, each sealing member 26a,b is preferably hermetically sealed to the open end of conduit 14a,b to seal it against contamination during shipping and handling, and preserve sterility of the conduit (and any associated fluid circuit) if it has been pre-sterilized. Each sealing member 26a,b is essentially as described above and may be of any suitable construction. In one preferred embodiment, the sealing member is in the form of a panel that includes a layer of conductive foil or film 28 that acts as a heating element, and the proximal surface of the laminate has a layer or coating or material 30 compatible with material at the conduit end. For a PP conduit end material, for example, the proximal layer or coating may be PP or other compatible material.

The sealing member 26a,b may be hermetically sealed to the open end of the respective conduit 14a,b by pressing the proximal side of the panel against the conduit open end and heating the foil by direct heat, induction, resistive, microwave, radiofrequency or ultrasound energy or other means until the end of the conduit and the proximal laminate layer melt sufficiently to bond or fuse together, sealing the interior of first the fluid flow circuit 14a,b. As explained earlier, the sealing member may also be attached by adhesive or other means suitable for the materials involved and the end use intended. After the sealing member is attached to the conduit, the conduit and associated fluid flow circuit 16 or 18 may, if desired, be sterilized in whatever manner is appropriate for the components of the circuit, such as steam, radiation, gas or other form of sterilization. In its broader respects, the present subject matter is not limited to medical fluid flow assemblies or to joining pre-sterilized fluid circuits or subassemblies. However, it is in the context of joining pre-sterilized fluid flow circuits or subassemblies to form sterile fluid flow assemblies (for medical and/or other fluid flow applications) where the present subject matter is expected to be particularly applicable.

As illustrated, both sealing members are multi-layer panels or laminates of essentially the same construction, and the end material of both conduits is preferably of the same material, such as PVC or PP, for example. While this may be preferred, it is not required. As noted earlier, the sealing members 26a,b may be identical or may differ. For example, only one sealing member may include a heating element such as conductive film or foil, as described earlier. Also, different materials may be used in the sealing members. It is also contemplated that the conduits may terminate in different materials and the conduits of each subassembly may comprise different materials at different locations. For example, the open end of a conduit may be of one material and the remainder formed of other materials, such as a PP for the end material and PVC for other portions.

Forming the Connection

FIGS. 4-9 diagrammatically illustrate how the fluid flow assemblies 16 and 18 are joined to form a sterile fluid flow assembly after they have been individually assembled and, if desired, pre-sterilized. Referring to FIG. 4, the conduits 14*a,b* may each be temporarily mounted on a respective welding or bonding fixture or holder (not shown in this figure) with the distal end of the conduit protruding from the fixture. The welding or bonding fixtures may be of any suitable particular configuration or material, but are preferably configured to coaxially align the open ends of conduits 14*a,b*, with the distal surfaces of the sealing members 26*a,b* (panels) in a face to face relation.

As illustrated in FIGS. 4 and 5, one or both of the welding fixtures are axially movable to bring the distal surfaces of the sealing members together into direct face to face contact and preferably to axially compress the ends of the fluid flow conduits 14*a,b* together. The compressive force (exemplified by opposed arrows in FIG. 5) employed will depend on the conduit materials, conduit thickness and device configuration, but it is contemplated that for conduits employing PVC or PP tubing of the size (e.g., ⅛-¼ inch OD) routinely found in disposable medical fluid flow systems, an axial force of about 1-1.5 pounds may be sufficient.

While held in contacting, face to face position, as illustrated in FIG. 6, the sealing members 26*a,b* are heated, such as by induction heating of the conductive foil or film 28 as described earlier, until the foil is heated sufficiently to melt the end material of the conduits. Induction heating may be carried out by any suitable induction heater and the metallic foil or film positioned at any suitable orientation to the magnetic field of induction coil, although a parallel relationship between the induction coil and foil (a perpendicular relationship between the magnetic field and the foil) may be most preferred. The power of the induction heater may depend on other variables, but for a flat coil of about 2.8 inches in diameter and having 20 turns, power from about 50 to 100 watts may be used at about 50 kHz and with a maximum current of about 4 A. This is but one example, however, and other electrical induction generators may be used as necessary for the particular configuration of sealing member and conduit involved. If carried out as a part of a sterile connection procedure, the elevated temperature is preferably high enough to sterilize the sealing members (or at least the relevant portion thereof that is exposed to the interior of the conduit) during the limited time that heating occurs. The elevated temperature may preferably be about 230° C. or higher such as 250-275° C., and more preferably about 260° C. or higher. This heating may preferably occur, for example, for about 5 or 6 seconds or less. Shorter heating times such as less than 4 seconds or 2 seconds and potentially even less 1 second, may be preferred to reduce operator time.

After or during heating, and while the conduit ends remain in a melted state, as best seen in FIGS. 7 and 8, the sealing members 26*a,b* (e.g., sealing panels) are simultaneously moved laterally from between the conduit ends. This may be done by moving either the sealing member or the conduit holders or both. This may be done manually or automatically. In the illustrated example, the conduits are held stationary and the sealing members pulled from between them. As the sealing members are pulled from between the ends of the conduits, the axial compressive force of the welding fixtures or conduit holders simultaneously and progressively forces the molten open ends of the conduits together in a face to face abutting relationship, and the molten ends of the conduits weld or fuse together. This preferably happens relatively quickly, such as 1-2 seconds or less.

In this illustration, the portion of the sealing member panel film or foil 28 that moves or slides over the open end of each conduit 14*a,b* is exposed to the environment inside the conduit. If the respective fluid subassembly is pre-sterilized, that portion of the sealing member is exposed to the sterile field inside the conduit. To prevent contamination, the earlier heating of the sealing member preferably raises the temperature sufficiently high not only to cause melting of the distal end of the conduit 14*a,b*, but also to sterilize the surfaces of the sealing member that are exposed to the sterile field inside the fluid circuit as the panel is pulled or dragged across the end of the tubing segment. This could be all the surfaces of the sealing member or just those surfaces, such as the metallic layer surfaces, that are exposed to the inside lumen or bore 15*a,b* of the conduit 14*a,b*. Thus, these surfaces do not contaminate the inside of the conduit, and the sterility of the conduit and any associated fluid circuit is maintained as the panel is pulled away from its original sealed position in order to expose the melted end of the conduit for contact with the opposed conduit. This happens simultaneously with each sealing member 26*a,b* of each subassembly 16 and 18, and the ends of the conduits 14*a,b* immediately engage and seal together as the sealing members are withdrawn, without contamination from the ambient environment—so the sterility of each fluid circuit is maintained.

After the sealing members are removed, the ends of the conduits are held together in compression by the holders while the connection is allowed to cool and the end material to harden. This requires only a short time, such as a matter of seconds for polymeric material. Fewer than 10 seconds, and even less, such as 7 seconds or less, may allow for sufficient cooling of PVC or PP conduit end material. As a result, the fluid flow assemblies 16 and 18 are joined in sterile manner with a permanent welded or fused junction or union 12, as seen in isolated view in FIG. 9. The flow circuit conduits may then be removed from the welding fixtures or holders and the resulting assembly or product is reading for use without further manipulation of the junction (as required in some prior art wafer systems), or for such further manufacturing steps as may be desired.

Connection Device

FIGS. 10-15 illustrate one version of a device or apparatus generally at 40 for carrying out the method described for making a connection, preferably in a sterile manner, between fluid flow conduits 14 or similar tubing of flow circuits or fluid flow subassemblies. In brief, the apparatus 40 includes two conduit holders 42*a,b*, power source 44 (seen in FIG. 10) and sealing member holder or puller 46, the operation of which may be automatically controlled by a controller employing, for example, a programmable microprocessor that is programmed to carry out the sequence of operations described below, or any appropriate part of them.

Figure 11:
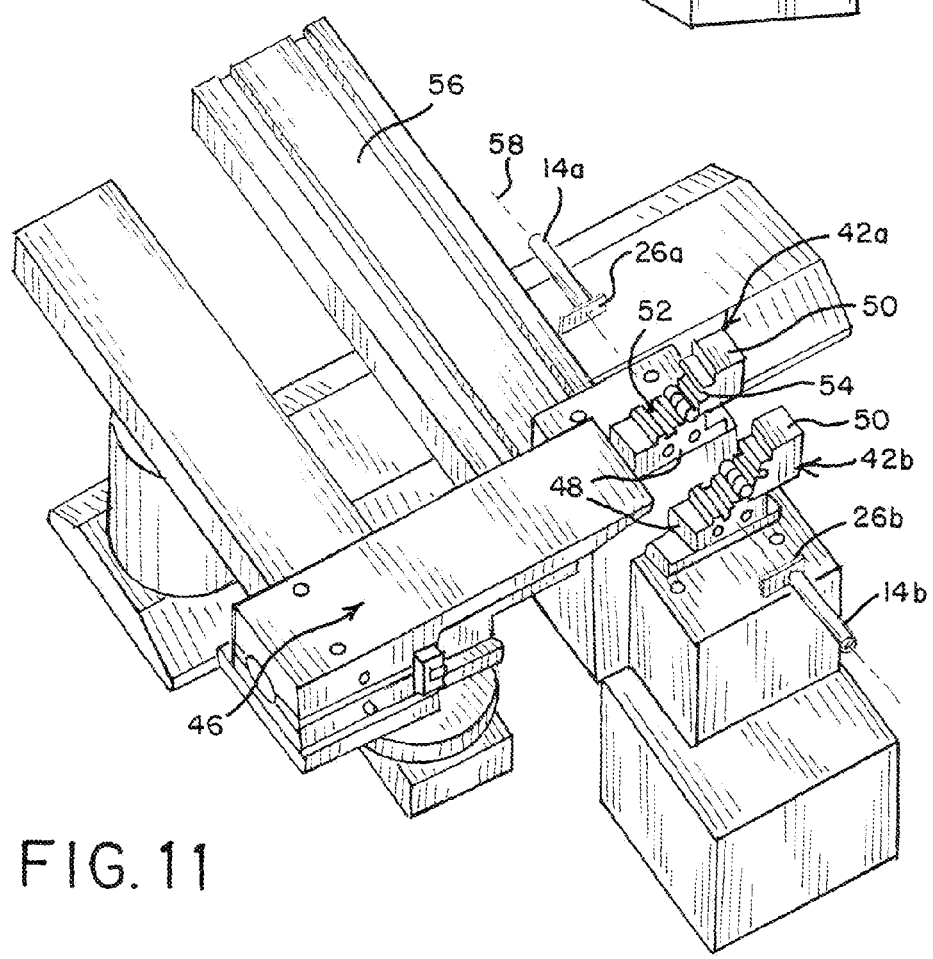
FIG. 11 is a top perspective view of the apparatus of FIG. 10.

The illustrated tube holders 42*a,b*, are each configured to clamp or grip a conduit 14*a,b* for movement toward and away from each other. As shown, each tube holder has a base 48 and clamp arm or jaw 50 pivotally mounted to the base and pivotal between a raised loading position, as shown in FIGS. 10 and 11 to allow positioning or insertion of conduits 14*a,b* into position for connection and a lowered clamping position (FIGS. 12-15) the conduit is clamped between the base and upper jaw.

Although the details may vary, in the embodiment illustrated, the base is configured with a jaw surface that includes an elongated slot or groove 52 for receiving a conduit 14a,b. The upper jaw or clamp arm 50 has a similar slot or groove 54. The slots or grooves 52 and 54 are in alignment or registration when the upper jaw is in the lower clamping position and are sized to annularly grip the conduit.

The tube/conduit holders 42a,b are relatively movable. As illustrated, conduit holder 42b is stationary and conduit holder 42a is mounted for linear movement along track 56, but both could be movable if desired. Tube holder 42a may be automatically or manually moved by any suitable apparatus, such as mechanical, electrical, hydraulic or pneumatic, for example a solenoid, stepper motor, gear drive, piston or other arrangement.

In any event, the tube holders 42a and 42b are preferably relatively movable between a first spaced apart position or station, where the conduits are loaded into the respective holders (see FIGS. 11 and 12), and a second more closely spaced connecting position or station (see FIGS. 13-15) where the connection is made. As seen in FIGS. 11-15 the conduit/tube holders 42a and 42b are positioned so that the conduits are held in axial alignment along center axis 58 and are relatively linearly movable toward and away from one another along that axis so that the conduits are maintained in axial alignment to achieve the eventual fusion connection.

FIG. 11 depicts the pair conduits 14a,b with attached sealing members 26a,b, being moved into position for loading into receiving slot or groove 52 in the respective conduit holder 42a and 42b. As described earlier, the illustrated conduits 14a,b may each be part of a larger fluid flow circuit or flow subassembly 16 or 18, as shown for exemplary purposes in FIG. 1, which are not shown in FIGS. 11-16 for purposes of simplicity and description only.

In the illustrated embodiment described earlier, each conduit 14a,b is attached to respective sealing member 26a,b in an off-set position. This allows a portion of the sealing member, such as a portion of the panel, to extend sufficiently laterally for gripping or holding. In the illustrated device 40, the sealing member holder or puller 46 is provided for grasping or gripping the sealing members. While such a sealing member holder 46 may take various configurations, in the illustrated device, the holder as illustrated is mounted laterally of the conduit holders at the connecting or sealing station.

Figure 12:
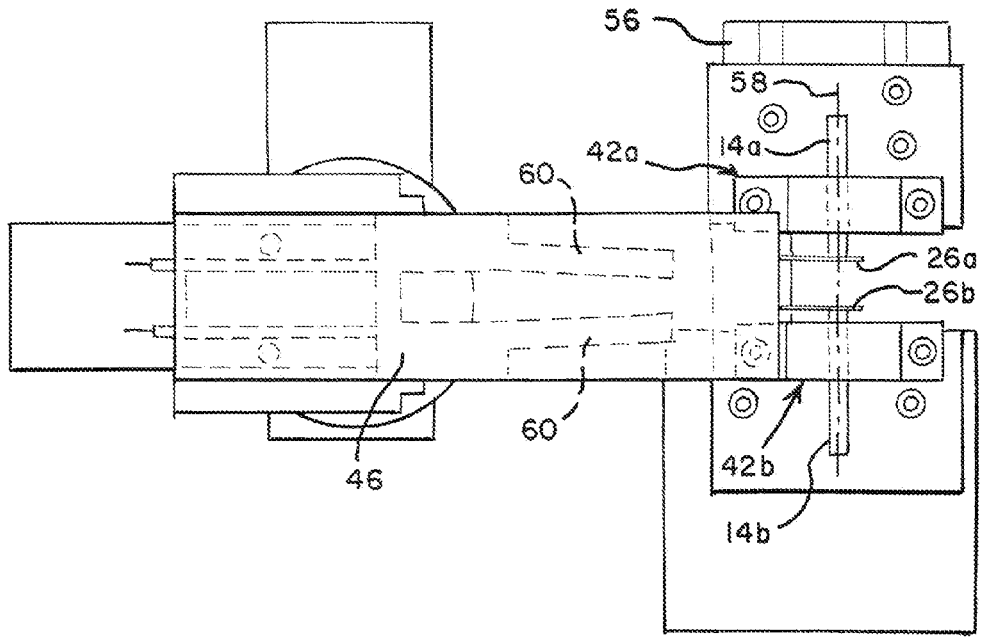
FIGS. 12-15 are partial top views of the apparatus of FIG. 10, illustrating sequential positions of the apparatus when connecting two fluid conduits.
Figure 13:
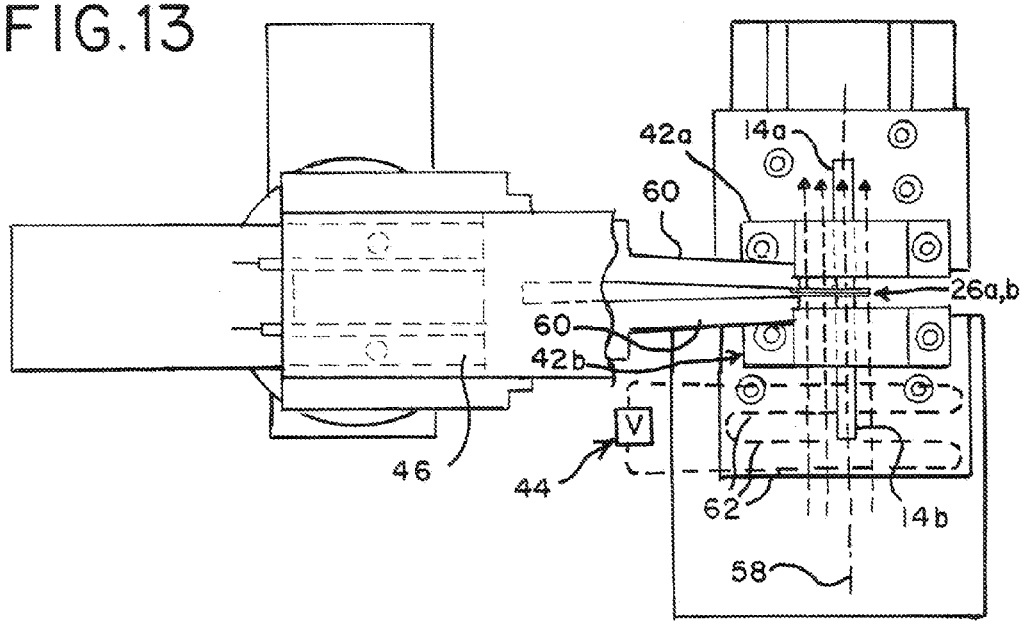
Figure 14:
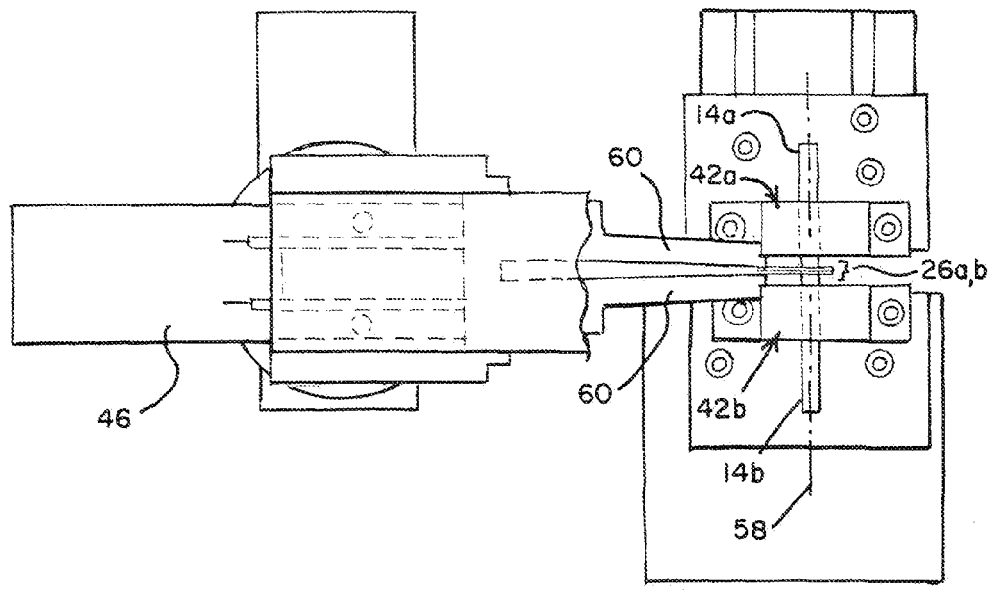
Figure 15:
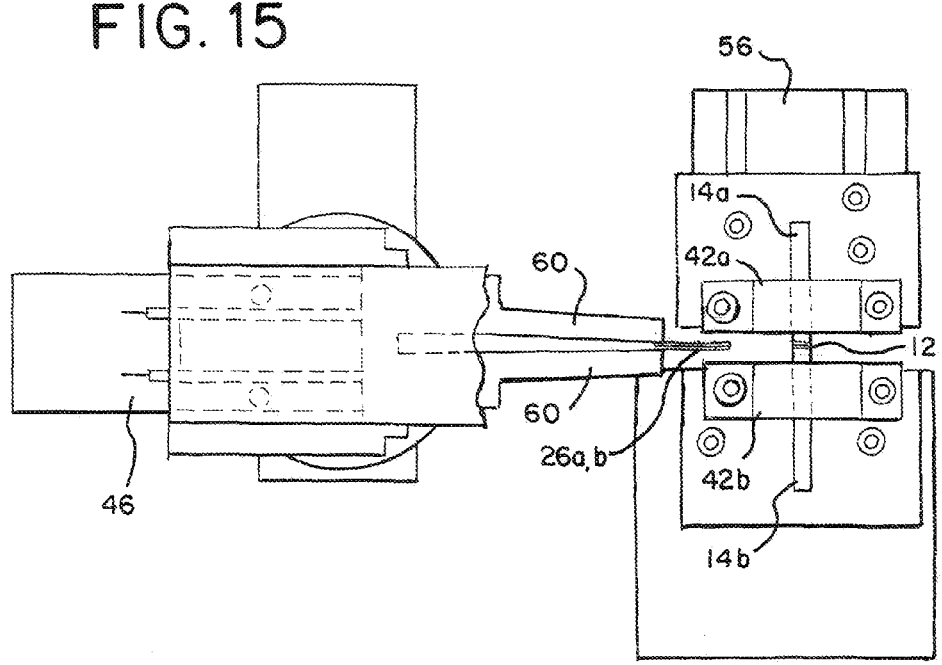

The conduits holders 42a,b and sealing member holder 46 are relatively movable and, as shown, the conduit holders are laterally stationary and the sealing member holder is movable between a first position laterally spaced from the conduit holders (FIGS. 10-12, 15) and a second position closer to the conduit holders for grasping or gripping the sealing members (FIGS. 13-14). The sealing member holder may be moved by any suitable means, mechanically, electronically, hydraulically, pneumatically, or manually such as solenoid, gear arrangement, piston, stepper motor or other.

As seen in more detail in FIGS. 10, and 12-15, the illustrated sealing member holder 46 has a pair of laterally extending pinchers or gripper arms or fingers 60. The pinchers are controlled, for example by any suitable mechanism (electrical, mechanical, hydraulic or pneumatic) or manually for operation between open spaced apart position (see, e.g., FIG. 12) and a closed pinching or gripping position (see, e.g., FIG. 13) for grasping the sealing members. As described earlier and below, relative lateral movement between the conduit holders 42a,b and the sealing member holder 46 moves the sealing members 26a,b from between the conduits 14a,b when the ends of the conduit are melted.

For heating the sealing members and melting the ends of conduits 14a,b, the device 40 also includes the power source 44 (FIG. 10). The power source may take the form or any suitable energy source, such as an electrical induction generator, direct voltage source, microwave generator, or other. In the illustrated embodiment, the heating element of the sealing member or members is heated by induction heating by inducing eddy currents in the heating element(s) by magnetic field generated by an induction generator. As illustrated, the eddy currents are induced in the heating element by a magnetic field generated by the flow of electricity in coils 62. Coils 62 are preferably positioned to generate lines of magnetic flux that intersect the heating element in a sealing member (e.g., flux lines perpendicular to a metallic film or layer 28 in the sealing member) to generate a current flow within the heating element that causes it to heat. As shown, the coils 62 are offset to one side of the sealing station. If the sealing station were located within the coils themselves, the power requirement for the induction generator could be considerably less. In the illustrated embodiment, one power source may be a 2.4 kW generator operated at about 200-300 A at about 200 KHz, such the Ameritherm EasyHeat 0224, from Ameritherm Inc. of Scottsville, N.Y.

The power source may employ any suitable electrical generator for creating eddy current flow within the heating element, but it may be preferred for the frequency of the current flow within the coils to be approximately matched to the thickness of the heating element. For example, as mentioned earlier, much of the induced electrical current in a conductor occurs within a limited thickness near the surface of the conductor, referred to as "one skin depth". The skin depth for a given material varies with the frequency of the inducing magnetic field. As examples, for an induction field having a frequency of about 200 KHZ, the thickness of one skin depth is about 14.6 μm (0.00057 inches) for copper and about 18.9 μm (0.00074 inches) for aluminum. Thus, having heating elements that are of particularly large thickness relative to the skin depth may be unnecessary and of diminishing effectiveness for induction heating, at a given frequency. In the present disclosure a heating element, such as a metallic layer or film, may be equal to or less than the skin depth. However, if such results in a metal layer that is too thin or fragile or otherwise unsuited for manufacturing or production purposes, the metallic layer may be of such thickness as is practical in those circumstances.

Use of Connection Device

Turning now to the method of making a sterile connection employing apparatus as shown in 10-15. FIG. 10 illustrates the device before any loading steps are taken. The conduit holder 42a and 42b are spaced apart in loading position and the sealing member holder 46 is spaced from the conduit holders.

FIG. 11 shows the conduits 14a,b being positioned into the conduit holders 42a,b, with the sealing members 26a,b in face-to-face relation. In this illustration, the sealing members 26a,b are in the form of relative thin panels such as webs or films, preferably a multi-layer panel, with one layer of at least one of the sealing members being a conductive metallic layer or foil that acts as a heating element.

FIG. 12, taken from above, shows the conduits 14a,b held in place in the conduit holders 42a and 42b, with the clamp jaws 50 lowered, and the holders still spaced apart in the loading position.

FIG. 13, shows tube holder 42a moved toward tube holder 42b, bringing the sealing members 26a,b together with the distal surfaces in face to face contact and exerting an axial compressive force on ends of the conduits 14a,b. In this figure, the sealing member holder 46 has moved into closer position, with a portion of the sealing members located between the grippers 60, which are shown in a pinching position. The dashed lines represent magnetic flux generated by coils 62 of the power source 44 to induce current in the heating member in at least one sealing member. The heating continues for a time sufficient to melt the open ends of both conduits 14a,b and preferably to sterilize the sealing members, or at least those portions of the sealing members that are exposed to the interior of the conduits when the sealing members are moved from between the conduit ends. Thus, if the conduits are pre-sterilized the sterile field therewithin will not be contaminated by pathogens from the sealing members.

The time and temperature of such heating will vary, depending on the materials selected, the magnetic flux and whether a sterile procedure is desired. For efficiency, it is contemplated that the heating may require a relatively short heating time. In a sterile connection situation the sealing members are preferably heated to a sterilization temperature such as at least 230° C. and preferably about 250-275° C., and at least 260° C. for about 2-5 seconds. It may be noted as this point that for a sterile connection, it is preferred that the material defining the open connection ends of the conduits have a melt point equal to or higher than the sterilizing temperature to better confirm sterility before the conduits are melted to form the junction or union 12.

After the polymeric ends of the conduits 14a,b has melted sufficiently, and before cooling, the sealing member holder 46 is moved laterally, pulling the sealing member panels 26a,b from between the conduits 14a,b. This action occurs relatively quickly, such as less than 1 or 2 seconds. The axial pressure exerted by the conduit holders 42a,b simultaneous presses the open ends of the conduits progressively together as the sealing members are pulled from between them, preventing ambient contamination of the inside of the conduits. The conduit holders continue to press the ends of the conduits together during cooling, and until the ends of the conduit fuse together and harden in a permanent fusion or welded junction 12. The time for cooling can vary depending on the conduit end material and temperature, and preferably is not longer than 5-10 seconds.

After cooling, the clamp arms 50 of conduit holders 42a and 42b are opened and the sealed conduits 14a,b may be removed from the holders, with a permanent connection or union 12 formed between them that allows fluid flow between the conduits without further user manipulation or processing.

Alternative Sealing Member/Conduit

Figure 16:
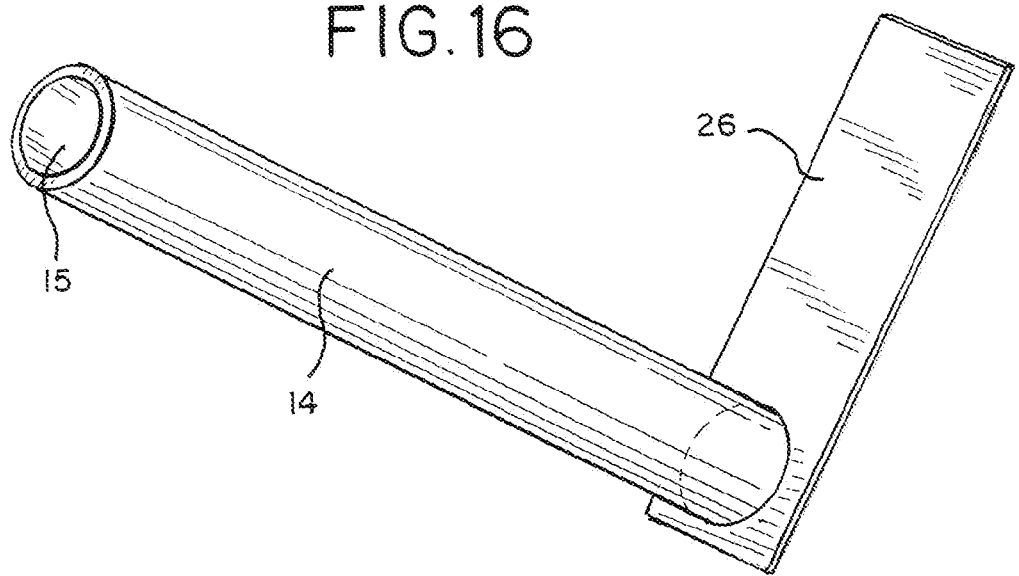
FIG. 16 is a perspective view of an end portion of a fluid conduit (which may be part of a larger fluid circuit or subassembly) sealed at the end by a sealing member in the form of a panel (which may be a web or film of one or more layers or coatings).
Figure 17:
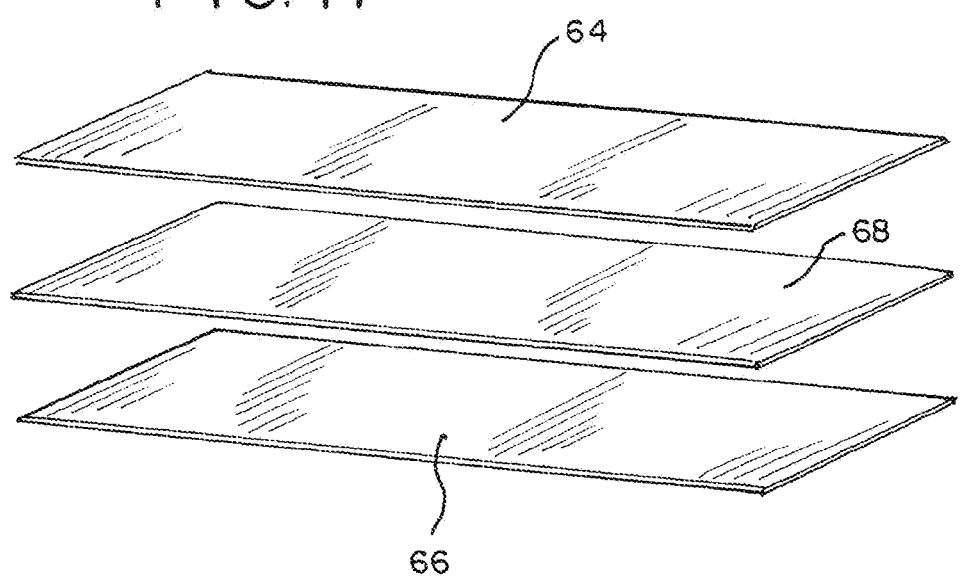
FIG. 17 is a perspective view of a multilayer embodiment of a sealing member panel that has three layers.

FIGS. 16 and 17 illustrate an embodiment of conduit 14a,b and sealing member 26a,b, that is presently contemplated as one possibly preferred configuration for sterile connection applications. As shown there, conduit 14a,b is a hollow tubular structure with an interior lumen or bore 15a,b and is made of a polypropylene (PP) material or other suitable material, which has a melt temperature preferably at or above sterilization temperature, which helps assure that sterilization temperatures have been reached and/or exceeded when the conduit is melted. The size of the tubing may vary as needed for the particular application. The illustrated sample has an inner diameter of about 4.1 mm and an outer diameter of about 6 mm.

The illustrated sealing member 26a,b is a triple-layer panel or web having outer layers of polymer, and a middle layer of electrically conductive metal or conductive polymer. More specifically, the proximal layer is of a material that is compatible with the material at the open end of the conduit, such PP and is preferably melt bondable to PP—for example for bonding to an open terminal end of conduit 14a,b in FIG. 16. As shown, this layer 64 is PP and, although thickness may vary, is illustrated with a thickness of about 0.05 mm. The distal polymer layer 66, is polyethylene terephthalate, and has a thickness of about 0.013 mm. The middle layer 68 is preferably metallic, electrically conductive and may be made of any of the materials identified earlier or alloys, and preferably a material exhibiting antimicrobial properties, as discussed in more detail later. The illustrated middle layer is an aluminum foil having a thickness of about 0.05 mm. The sealing member 26a,b of FIG. 17 is heat bonded to the open end of conduit 14a,b by direct heat weld of the PP layer to the PP conduit to hermetically seal the open end of the conduit.

It is noted that many medical fluid flow systems use PVC tubing. If PP is used as the material at the end of the fluid flow conduit 14a,b, it may be necessary to provide a connection transition member or other arrangement between the PP conduit and PVC tubing due to certain material incompatibilities between PVC and PP. Such a transition member may take any suitable configuration without departing from the present disclosure.

The conduit/sealing member assembly of FIGS. 16 and 17 is believed to be of particular use in providing sterile connections using the method and apparatus described earlier. Specifically, when the heating element (middle layer 68) of the sealing member is heated to at least about 230° C., such as 250-275° C. and preferably at least about 260° C. for at least 2 seconds and preferably at least 3 or 4 seconds, sterile connections can be formed between molten PP conduit end material. After cooling, the conduit is immediately ready for fluid flow without the need to manipulate the junction or union 12, as is required for other systems.

Alternative Embodiment

FIG. 18 illustrates one example of a fluid circuit assembly 70, including a connection assembly 72 joining two fluid flow circuits or subassemblies 74 and 76 to form the fluid circuit assembly 70. Each fluid circuit or subassembly 74 and 76 may include additional tubing, containers, valves, separation chambers, and other selected fluid processing or storing apparatus, not shown, as desired for a particular application or end use. In its broader aspects, this embodiment is not limited to making sterile connections. However, it will be appreciated that it has particular application and benefit in making sterile connections between pre-sterilized components, flow circuits or subassemblies of a sterile fluid flow assembly or system, such as a disposable sterile medical fluid flow assembly.

More specifically, FIG. 18 illustrates a fluid circuit assembly in the form of a disposable flow system 70 which comprises at least two flow circuits or subassemblies that may be pre-sterilized and, more specifically, at least a first fluid flow circuit 74 and a second fluid flow circuit 76. As noted above, it is within the scope of this description that the first and second circuits 74 and 76 may include additional parts or pieces of the overall system assembled in any desired way.

Turning to FIG. 20, which is inverted relative to FIG. 18, the portion of the first fluid circuit or subassembly 74 shown in the drawings includes tubing 78, housing 80, terminal tubing segment 82 and a sealing member 84. The tubing and tubing segment are hollow for the flow of liquid therethrough, and may be formed of any suitable material such as a flexible resilient material, such as PP or PVC or other thermoplastic material or other plastic that also preferably lends itself to bonding to the housing and/or sealing member, such as by melt or fusion or adhesive bonding. The tubing 78 and tubing segment 82 need not be of the same material, but it is generally preferred for reasons evident later that at least the tubing segment be pliable and resilient.

The housing 80 may be of any suitable configuration or shape. As shown for purposes of illustration only, the housing is made of rigid material, such as rigid plastic for disposability and tubing bonding purposes. The illustrated housing is generally oval with a flat wall 86 and depending side wall 88 that together define an internal recessed area or volume, which may be temporarily sealed or protected by a removable cover (not shown), such as a dust cover sealed to the lower edge of the side wall. For fluid flow therethrough, the housing has a generally L-shaped fluid passageway 90 with an inlet for attachment of tubing 78 and an outlet within the recessed area for attaching the terminal tubing segment 82. Together, the tubing, housing and tubing segment form a fluid flow conduit of the first circuit 74 that, as explained in more detail below, is to be attached, preferably in a sterile manner, to a fluid flow conduit of the second fluid flow circuit 76.

Turning now to the sealing member 84, "sealing member" is, as described earlier, not limited to a single element or layer, but can be an assembly of multiple parts and pieces, including a heating member or element (which likewise can be more than one part or piece).

For reference purposes only, the side of the sealing element or panel 84 that faces the terminal tubing segment 82 to which it is attached is referred to as proximal, and the side or surface facing away from the tubing segment is referred to as distal. As presently contemplated, the proximal surface of the panel 84 or a portion of the proximal surface includes a layer or coating of a material that is compatible with and suitable for bonding to the terminal tubing segment 82 in order to seal the open end of the tubing segment. For example, the panel may include a PP or PVC layer or coating that can be directly bonded to PP or PVC of the tubing segment. If the tubing segment 82 is made of other material, a coating or layer of different material may be required. There may also be one or more intermediate layers between the proximal layer or coating that bonds to the tubing segment and the conductive layer, and/or there may be additional layers or coatings distal of the conductive layer as well. In general, the earlier description of the sealing member is equally applicable here, and will not be repeated in its entirety.

The illustrated sealing member (e.g., panel 84) is of elongated oval shape and bonded to the terminal tubing segment 82 near one end of the panel. The remaining portion of the panel extends from the terminal tubing segment into the recessed area of the housing 80. As explained in more detail below and shown in FIGS. 19, 20, 22 and 23, the housing includes an elongated access port 92 that allows access to the panel by an actuating member for moving the panel, after or during heating but preferably while the foil is still hot and the plastic tube segment end is molten, from a sealed and closed position (FIGS. 19, 20 and 21) covering the open end of the terminal tubing segment, to a non-sealing, open position (FIGS. 22, 23 and 24), separated from the tubing segment and exposing the open end of the tubing segment. For cooperation with such an actuating member, the panel may include an aperture 85 aligned with the access port to allow insertion of the actuating member finger or pin through the port and into the aperture.

The illustrated fluid conduit of the second fluid flow circuit 76 is constructed generally similarly to that of the first flow circuit 74 described above, and includes tubing 96, housing 98, terminal tubing segment 100 and sealing member 102 in the form of a panel (e.g., a laminated film or web) bonded or otherwise sealably attached to the open end of the tubing segment 100 to seal it closed. The housing 98 has an internal L-shaped flow path 104 with an inlet port for attachment to tubing 96 and an outlet port for attachment to the terminal tubing segment 100.

The sealing member (panel) 102 as shown is essentially the same as the sealing member 84 of the first fluid flow circuit, although they may differ, and only one may contain a heating member or element if desired. The sealing member or panel 102 is attached to the terminal tubing segment 100 in the same manner as described with respect to flow circuit 74.

The housing 98 of the second fluid flow circuit 76 may be of any suitable configuration, but in the illustrated embodiment is of rigid plastic material and configured for attachment to the housing 80 of the first fluid flow circuit—preferably an irreversible attachment. "Irreversible attachment" means attachment in a manner that prevents separation in the normal course of usage and handling, and maintains attachment except upon application of unusually large and potentially destructive forces or manipulation not normally encountered in routine use. The housing 98 is generally oval and has a flat upper wall 106 and a depending side wall 108 that defines a recessed area or region therewithin, which can be covered by a closure or dust cover, not shown. The housing 98 is sized so that it is slightly smaller than housing 80 and can be inserted into housing 80. For irreversible attachment the housings 80 and 98 have interfering surfaces that engage to prevent separation as described above. Specifically, as shown for illustrative purposes only, side wall of housing 98 has opposed flexible fingers 110 with end hooks or flanges 112 that snap or otherwise fit into receiving apertures or slots 114 in the housing 80 to prevent separation in normal usage.

As best shown in FIGS. 18-20, the housings 80 and 98 are configured and dimensioned so that when attached, the distal surfaces of the sealing members or panels 84 and 102 are pressed into direct face to face contact. Also, the resilient terminal tubing segments 82 and 100 are located in opposed coaxial registration with one another, with at least one of the tubing segments and preferably both being compressed sufficiently that when the sealing members are removed from between them, the tubing segment(s) expand into direct end-to-end contact. This face to face positioning of the sealing members also allows an actuating member to extend through housing access port 92 and the apertures 94 in both sealing members so as to move both sealing members 84 and 102 simultaneously upon heating and melting of terminal end segments 82 and 100.

As noted above, preferably the tubing segment or segments 82 and 100 are compressed sufficiently so that when the sealing members or panels 84 and 102 are heated (as by induction, microwave, direct voltage application or other) to sterilizing temperature and the tubing segments distal ends melted, and the sealing members are pulled laterally from between the segments, the segment(s) expand from the compressed position and the molten open ends of the tubing segments press together progressively under pressure from the inherent resiliency of the tubing segment material and fuse or weld together to form a generally permanent junction or union between the flow paths of the two fluid flow circuits (see FIG. 24). This is carried out relatively quickly and the junction or union is formed without exposure of the inside of the sterile fluid circuits to ambient atmosphere that would render them non-sterile, thereby providing, in preferred form, a novel and highly functional and efficient sterile connection device and method suitable for joining pre-sterilized fluid circuits or subassemblies to create sterile assemblies thereof. As can be seen in these figures, the sealing members are enclosed in their respective housings prior to attachment of the housings together and are enclosed within the attached housings both in the closed position (FIG. 20) and in the open position (FIG. 23), which reduces waste handling and simplifies functionality.

FIG. 25 illustrates the housing connection assembly 70 in combination with a mounting or receiving fixture 116. Fixture 116 may be of any desired configuration and/or associated with any desired apparatus or piece of equipment. The fixture 116 has a slotted receiving station or recess that generally corresponds to the shape of the assembled housing. The fixture may be attached to another apparatus, such as a blood processing centrifuge used by blood banks and the like (e.g., the Fenwal Alyx or Amicus systems) or may be part of a sealing apparatus that is devoted to making sterile sealed junctions between fluid processing components (as in the Terumo SCD Device) or may be part of a manufacturing system for use in more basic manufacturing processes that assemble systems for subsequent consumer usage. In any event, it is contemplated that the fixture 116 has an electrical induction coil or microwave antenna built into it or into other apparatus in close proximity to it, for induction or microwave heating of the sealing members 84, 102. If resistive heating is employed via direct voltage contacts, the fixture could have voltage contact points that are wired via the housing to the heating element in one or both of the sealing members.

In addition, the fixture or associated apparatus could include an actuating member that extends through access port 92 of the housing to provide automated movement of the sealing member panels (laminates) from the closed position shown in FIG. 20 to the open position shown in FIG. 23, although it should be noted that manual actuation is also possible. If part of an automated operation, the fixture and/or related apparatus could include a timer, temperature sensor and any associated control circuitry or programmable processor for actuating the heating of the sealing members and moving the sealing members to expose the open ends of the flow circuit (the open ends of the tubing segments) and form the sterile union between the circuits.

Assembly Method of Alternative

The method of making the fluid flow circuit assembly 70, preferably by sterile connection of two pre-sterilized fluid flow circuits or subassemblies, is one of the particularly beneficial aspects of the present subject matter. The method may be used in any suitable environment, such as in a manufacturing facility in the course of manufacturing a product for commercial sale, on-site to allow the customer or user to join product components in such a configuration as desired, or for other purposes. The resulting flow circuit assembly may be for medical fluids, including blood, intravenous solutions such as saline or dextrose, sterile water, anticoagulants, blood component preservatives, or any other desired fluid. In broader respect, the fluid could even be a gas.

Referring to the drawings, which represent one example of how such fluid flow circuits may be joined, the fluid flow circuit assembly 70 is preferably formed by sterile attachment of the pre-sterilized fluid flow circuits or subassemblies 74 and 76, which may require different sterilization or production processes as described earlier or which may be separately produced and sterilized for other reasons. As described above, the pre-sterilized flow circuits 74 and 76 each include a flow conduit in the form of tubing 78, 96, a housing flow path 90, 104 and terminal tubing segment 82, 100. The terminal ends of the flow conduits, i.e., the material of the terminal end segments, are of a heat meltable material, such as PP, PVC or other thermoplastic polymeric material. Each circuit or subassembly also includes a sealing member 84, 102, shown in the form of a thin panel, such as a multi-layer web or film that is attached to the terminal end tube segment and seals the open end of the respective flow conduit. In the illustrated example, the sealing member is hermetically sealed to the end segment to maintain the inside of the respective fluid circuit sterile. At least one and preferably both of the sealing members include a heating element, such as a metallic foil or film described earlier.

To join the fluid flow circuits in a sterile manner, any dust cover is removed from the housing housings 80 and 98, and the housings are irreversibly attached, such as by inserting housing 98 into housing 80 until the side hooks 112 snap into slots or apertures 114. In this position, the distal surfaces of the sealing members (e.g., the distal surfaces of the panels) are in direct face-to-face contact, as seen in FIGS. 20 and 23, and one or preferably both of the tubing end segments 82, 100 are compressed.

The assembled housing or connection assembly 72 may then inserted into the receiving slot of fixture 116. Preferably each sealing member is then heated by an energy source such as an induction coil positioned to create a magnetic field that causes induction heating in the heating element or elements. The induction coil is preferably energized with a suitable alternating current for a time sufficient to heat the heating element film or foil to a sterilizing temperature, which also serves to melt the ends of the tubing segments 82, 100. The conductive film or foil is preferably raised to a temperature sufficient to sterilize at least the surfaces of the laminates and/or film or foil that may be exposed to the sterile field within each of the fluid flow circuits, and specifically the foil or film is preferably heated to at least about 230° C. and preferably 250-275° C. and more preferably at least about 260° C. Depending on the power of the induction heating coil or other energy source and location relative to the heating member film or foil, it is anticipated that less than 10 seconds and preferably less than 5 seconds will be needed to raise the temperature to sterilize the desired surfaces. Because it occurs so quickly, this may be referred to a "flash heating." At such temperature, it is understood that only limited time, e.g., less than a few seconds and preferably less than a second (or on that order of magnitude), is required to sterilize the surfaces of the panel and/or film or foil. If only one sealing member has a heating element, that element will also serve to heat and sterilize the other sealing element.

As the heating element(s) are heated to preferably sterilize the surfaces of the sealing members, the material of the terminal end segments 82, 100 of each fluid circuit is also simultaneously heated. More specifically, the terminal end segments are heated by the heating element beyond their melt temperature, causing melting of at least at the terminal end edges of the tube segments. If the segments are made of PVC, such melting will typically occur at about 176° C. or above. If higher temperatures are desired for better assurance of sterilization, other materials may be selected for the terminal end segments of the fluid flow paths—such as polypropylene.

After the surfaces of the sealing members/foil or film are sterile, if desired, and the terminal end segments melted, the sealing members 84, 102 are simultaneously moved or pulled laterally from between the facing end segments. In an automated system, this could be done relatively quickly and smoothly by a movable pin or finger that extends through the access port or slot 92 and into aligned apertures 94 in each sealing member. The pin or finger movement could be automatically controlled by a solenoid or other such device, or it could be done manually if desired. As noted earlier, this motion drags each sealing member panel across the open end of the respective tubing segment, which exposes a surface of the panel or foil to the lumen within the respective fluid flow circuit. However, if heated sufficiently, such surfaces have been sterilized and because they are still hot when pulled from between the tubing segments, they remain sterile and do not contaminate or destroy any sterility of the fluid flow circuits. Also, because at least one (preferably both) of the resilient terminal end segments 82, 100 of each of the fluid flow circuits is compressed when the housings are connected, they (or at least one of them) simultaneously expand into direct end-to-end contact with one another as the hot sealing members are pulled from between them, and the molten end edges of the terminal segments are progressively pressed together, without exposing the interior of the fluid flow circuits to non-sterile ambient atmosphere, and immediately fuse or weld together to form a permanent junction or union between the fluid flow circuits.

The connection apparatus and method described above have several safety and reliability benefits in addition to those apparent from the above description. Although the material of the end segments cools relatively quickly, the surrounding housing 80, 98 protects the junction against inadvertent user contact, touching or other interference with the sealing process. Also, each terminal end tubing segment 82, 100 is isolated from its respective tubing 78, 96 and the remainder of the fluid circuit by one of the rigid housings 80, 98. Thus, user movement or jostling of the tubing 78, 96 is isolated from the sterile junction. As noted earlier, the operation of the system can be visually confirmed, if desired, by viewing the location of the sealing members through the access port or slot 92.

The fluid circuit assembly is now ready for transfer of liquids between the circuits or subassemblies, and if the fluid circuits were pre-sterilized, sterility has been maintained. No parts or pieces remain for user disposal and no expensive wafer is required.

Another Alternative Embodiment

FIGS. 26 and 27 shows another embodiment that accommodates manual movement of the sealing members. More specifically, FIG. 26 shows first and second fluid flow circuits or subassemblies 120, 122 to be joined. The fluid flow circuits are preferably pre-sterilized and joined in a manner that preserves sterility. Fluid flow circuit 120 includes tubing 124, rigid housing 126, heat meltable terminal tubing segment 128 and sealing member (panel) 130 sealing the end of the terminal tubing segment. The housing 126 has an internal fluid flow path 132 with an inlet for attachment to tubing 124 and an outlet for attachment to the terminal tubing segment 128.

Similarly, fluid flow circuit 122 includes tubing 134, rigid housing 136, heat meltable terminal tubing segment 138 and sealing member 140 sealing the end of the terminal tubing segment. The housing 136 has an internal fluid flow path 142 with an inlet for attachment to tubing 134 and an outlet for attachment to the terminal tubing segment 138.

The housings 126, 136 are configured to be joined in preferably irreversible attachment as shown in FIG. 27. In the configuration shown there, the housings have complementary barbs and recesses that engage when the housings are pushed together and preferably prevent disconnection under ordinary usage conditions.

At least one of the sealing members 130, 140 includes a heating member and, as preferred, the sealing members are identical thin multi-layer panels having metallic foil on or near the distal surface and a material sealingly attachable to the terminal tubing segment on the proximal surface. The earlier discussion regarding sealing members applies equally to this embodiment.

The housings 126, 136 are configured and dimensioned so that when the housings are attached, the distal surfaces of the sealing members are brought into direct face-to-face contact. At least one and preferably both of the terminal tubing segments are pliable and resilient, and compressed by the housings when the housings are attached. The heating elements of the sealing members are then heated, such as by inductive heating or resistive heating, preferably until they reach sterilizing temperature for sufficient time to effect sterilization of the surfaces of the sealing member (for example 260° C. or higher). This also results in heating of terminal tubing segments, raising at least the end portions of the segments above their melt temperature, to a molten state. At that time, the induction heating may be terminated and the sealing members are simultaneously gripped and pulled rapidly, while still hot, from between the tubing end segments. Because the portions of the sealing member panels that are pulled across the open end of the tubing segment are sterile and preferably still hot, they do not result in contamination of either of the flow circuits. As the panels exit from between the tubing segments, the molten end edges of the tubing segments are forced simultaneously progressively together due to the compression caused by the housings, and the molten ends of the face-to-face tubing segments fuse or weld to form a sterile permanent union or junction between the circuits.

Antimicrobial Enhancement

In accordance with another aspect of this subject matter, the sterilizing/welding process time herein can be reduced in any of the above apparatus, systems and methods employing sealing members that have antimicrobial properties in whole or in pertinent part. Employing sealing members with surfaces having significant antimicrobial properties can, in theory, reduce sterilization heating times by as much as 50% or more as compared to other types of sealing members.

Antimicrobial surfaces potentially prevent or retard the growth of bacteria, viruses and fungi. While various materials may have antimicrobial properties, certain metals or metal alloys, including conductive metals that are particularly useful in the present subject matter, have significant antimicrobial properties. These metals include silver, copper, brass, stainless steel, titanium dioxide and alloys thereof, particularly silver and copper.

In the present subject matter, the sealing members may have all or a portion of its surface or heating element or member made of material having antimicrobial properties— particularly that portion of the surface that is exposed to the inside of the attached fluid conduit. This portion of the surface is typically the surface that is exposed to the inside of the conduit while the sealing member is attached to the conduit and that is exposed to the inside of the conduit as the sealing member is moved from between mating conduit ends during the sterile sealing process. Alternatively the entire proximal surface of each sealing member (which is the surface that faces the conduit to which it is attached) or the entire proximal and distal surfaces of the sealing members could have antimicrobial properties.

In one implementation, a sealing member could be a single layer or foil of uncoated or bare metal having antimicrobial properties, such as copper or copper alloy. Alternatively, the sealing member could, if desired, be a laminate with the requisite surfaces having antimicrobial properties. For example, such a laminate could, if desired, include a metallic proximal surface and metallic distal surface with an intermediate layer of polymer adhesive or other material.

In one preferable aspect, the sealing member is a single layer of metal foil or film, with bare and uncoated proximal and distal surfaces for full antimicrobial effect. The flow conduit of a fluid circuit or fluid circuit subassembly could be attached to the sealing member by applying a suitable adhesive to the open end of the conduit and pressing the sealing member and conduit together until the adhesive cures. Thus, all the surface of the sealing member exposed to the ambient atmosphere is bare exposed metal, such as copper, silver or other antimicrobial material, that exhibits inherent antimicrobial properties for substantially preventing or retarding the growth of bacteria, viruses and/or fungi. Such properties may automatically provide a several log reduction of contamination load or bioburden on the sealing member surfaces. The same may also be said of that portion of the sealing member that is fully enclosed within the open end of the attached conduit. That portion, however, is typically pre-sterilized with the inside of the attached fluid conduit and maintained sterile by the bond with the open end of the conduit. The other portions of the sealing member are exposed to potential contamination from the ambient atmosphere and the antimicrobial properties of significant benefit.

Sterilization in medical applications typically requires about a six log reduction in microbial burden. If the exposed surfaces of the sealing member provide, by way of inherent antimicrobial effect, for example, a three log reduction, it is only necessary for the induction or other heating that is used in the sterilizing/welding to provide the remaining three log reduction to achieve satisfactory sterilization—significantly reducing the amount of time required to achieve sterilization—potentially by fifty percent (50%) or more, such as sixty-six percent (66%). Such sealing members exhibiting increased antimicrobial activity could be used with any of the assemblies, subassemblies, methods or apparatus described herein.

Although described in terms of preferred and alternative embodiments for purposes of illustration, it is understood that other variations are within the scope of this disclosure. Such changes or variations may include, without limitation, changes in shape, configuration, timing, materials, pressures and the like as would be apparent to a person skilled in the field upon reading this description.

The invention claimed is:

1. A method of joining first and second fluid flow circuits to form a fluid flow circuit assembly, each fluid flow circuit including a fluid flow conduit with a lumen and an open end terminating in a polymeric material and a sealing member attached to the flow conduit and sealing the open end thereof, and at least one of the sealing members including at least one single-use heating element as a pre-assembled composite part of the sealing member prior to joining;
   (a) melting the polymeric material of the open ends by heating the at least one heating element;
   (b) relatively separating the sealing members and the respective open ends to which they are sealed to expose the open ends; and
   (c) bringing the exposed open ends together while melted to form a junction between the fluid flow circuits that allows fluid flow therebetween.

2. The method of claim 1 wherein each of the sealing members comprises a panel attached to the open polymeric end of the respective conduit and at least one of the panels comprises a metallic layer defining the heating element, the method including:
   positioning the polymeric ends of the conduits generally in axial alignment and with the respective panels in face to face contact,
   heating the metallic layer sufficiently to melt the polymeric material of the open end of each conduit,
   separating the sealing members and the open ends by laterally separating the panels from between the polymeric ends while the polymer is melted while applying an axial compressive force to the conduits so as to substantially simultaneously bring the open ends together as the panels are separated from between the conduits; and
   cooling the molten ends while maintaining the axial compressive force to form a junction between the fluid conduits that allows fluid flow therebetween.

3. The method of claim 2 in which the conduits are held generally laterally stationary during heating and the panels are moved laterally from between the conduits.

4. The method of claim 2 in which the metallic layer is electrically conductive and heated by an inductive electrical power source operating at a selected electrical frequency and the metallic layer has a thickness not substantially greater than the skin depth for such metal at such frequency.

5. The method of claim 2 in which the fluid flow circuits are pre-sterilized, and the panels and the open ends are separated relative to one another and the melted ends are compressed together while maintaining the sterility of the fluid flow circuits.

6. The method of claim of 2 in which the metallic layer comprises a material that exhibits an antimicrobial property.

7. The method of claim 2 in which the metallic layer is heated to at least sterilizing temperature for a time sufficient to sterilize the sealing members before moving the panels relative to the open ends.

8. The method of claim 2 in which the polymeric material has a melt temperature of about 230° C. or greater.

9. The method of claim 2 in which each of the first and a second fluid flow circuits comprises a panel having a plurality of layers including a polymer layer and a metallic layer defining the heating element.

10. The method of claim 2 in which at least one of the fluid flow circuits comprises a panel having a plurality of layers including two polymer layers and a metallic layer defining the heating element located between the polymer layers.

11. The method of claim 2 wherein the panel has a thickness of less than about 0.5 mm.

12. The method of claim 1 including sterilizing each of the first and second fluid flow circuit prior to steps (a)-(c).

13. The method of claim 1 wherein the at least one heating element is heated to a sufficient temperature for a time sufficient to sterilize the sealing members.

14. The method of claim 1 wherein the at least one heating element is heated to at least about 230° C.

15. The method of claim 1 wherein the at least one heating element is electrically conductive and is heated by induction.

16. The method of claim 1 wherein at least one of the sealing members comprises a metallic film defining the at least one heating element.

17. The method of claim 1 wherein at least one of the sealing members is heated by an inductive electrical power source operating at an electrical frequency of "f" and the at least one member includes a metallic film having a thickness not substantially greater than the skin depth for such metal at such frequency.

18. The method of claim 1 wherein at least the surface of the sealing member that is exposed to the interior of the fluid conduit comprises a material having antimicrobial properties.

19. The method of claim 1 wherein the fluid flow circuits are pre-sterilized and the sealing members and open ends are relatively separated and the melted ends are compressed together while maintaining sterility of the fluid flow circuits.

20. The method of claim 1 wherein the open end and sealing member of each fluid flow circuit are carried by a housing configured for connection to the housing of the other fluid flow circuit.

21. The method of claim 1 wherein each of the sealing members comprises a film including a metallic layer attached to the open polymeric end of the respective conduit, the method including:
- positioning the circuits with the open polymeric ends of the conduits generally in alignment and with the respective films in face to face contact,
- heating the metallic layer sufficiently to melt the polymeric material of the open end of each conduit and sterilize the sealing members,
- separating the films from the respective open ends by laterally withdrawing the films substantially simultaneously from between the molten polymeric ends while pressing the open ends of the conduits together; and
- cooling the open ends while maintaining the pressure, forming a junction between the fluid conduits.

22. A method of joining first and second fluid flow conduits, each having a lumen and an open end terminating in a polymeric material and a sealing member attached to the flow conduit and sealing the open end thereof, and each of the sealing members including at least one single-use heating element as a pre-assembled composite part of the sealing member prior to joining, the method including:
(a) placing the sealing members in face to face contact;
(b) melting the polymeric material of the open ends by heating the at least one heating elements of each sealing member;
(c) separating the sealing members from the respective open ends by withdrawing the sealing members from between the respective open ends of the conduits while pressing the open ends of the conduits toward each other to bring the exposed open ends together while melted to form a junction between the fluid flow conduits that allows fluid flow therebetween.

23. The method of claim 22 wherein each of the sealing members comprises a panel attached to the open polymeric end of the respective conduit and each of the sealing members comprises a panel having a plurality of layers including a polymer layer and a metallic layer defining the at least one heating element, the open polymeric end of the respective conduit being sealingly attached to the polymer layer, the method including:
- positioning the polymeric ends of the conduits generally in axial alignment and with the respective panels in face to face contact,
- heating the metallic layers sufficiently to melt the polymeric material of the open end of each conduit,
- laterally separating the panels from between the polymeric ends while the polymer is melted to expose the open ends and while applying an axial compressive force to the conduits so as to substantially simultaneously bring the exposed open ends together as the panels are separated from between them; and
- cooling the melted ends while maintaining the axial compressive force to form a junction between the fluid conduits that allows fluid flow therebetween.

24. The method of claim 23 in which the heating element is heated by an inductive electrical power source operating at a selected electrical frequency and the heating element has a thickness not substantially greater than the skin depth for such metal at such frequency.

25. The method of claim 22 in which the conduits are pre-sterilized, and the melted ends are joined while maintaining the sterility of the conduits.

26. The method of claim of 22 in which the sealing member comprises a material that exhibits an antimicrobial property.

27. The method of claim 22 in which the heating element is heated to at least sterilizing temperature for a time sufficient to sterilize the sealing members before separating them relative to the open ends.

28. The method of claim 22 wherein each sealing member includes a panel having a thickness of less than about 0.5 mm.

* * * * *